US008834422B2

(12) United States Patent
Walker et al.

(10) Patent No.: US 8,834,422 B2
(45) Date of Patent: Sep. 16, 2014

(54) VASCULAR ACCESS ASSEMBLY AND SAFETY DEVICE

(71) Applicant: Covidien LP, Mansfield, MA (US)

(72) Inventors: Sandra A. Walker, St. Charles, MO (US); Kevin R. Martz, Desoto, MO (US); Brian P. Sharp, Johnston, RI (US); Gregory A. Steube, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/651,979

(22) Filed: Oct. 15, 2012

(65) Prior Publication Data

US 2013/0096504 A1    Apr. 18, 2013

Related U.S. Application Data

(60) Provisional application No. 61/547,410, filed on Oct. 14, 2011.

(51) Int. Cl.
*A61M 5/178* (2006.01)
*A61M 25/06* (2006.01)
*A61M 5/32* (2006.01)

(52) U.S. Cl.
CPC ......... *A61M 25/0618* (2013.01); *A61M 5/3273* (2013.01); *A61M 25/0606* (2013.01)
USPC .................................. 604/164.01; 604/164.08

(58) Field of Classification Search
USPC ................. 604/110, 164.01–164.08, 192–198
See application file for complete search history.

(56) References Cited

U.S. PATENT DOCUMENTS

| 3,134,380 | A | 5/1964 | Armao |
| 3,884,230 | A | 5/1975 | Wulff |
| 4,387,879 | A | 6/1983 | Tauschinski |
| 4,512,766 | A | 4/1985 | Vailancourt |
| 4,725,267 | A | 2/1988 | Vaillancourt |
| 4,755,170 | A | 7/1988 | Golden |
| 4,778,453 | A | 10/1988 | Lopez |

(Continued)

FOREIGN PATENT DOCUMENTS

| WO | WO 2010/061405 | 6/2010 |
| WO | WO 2011/036574 | 3/2011 |
| WO | WO 2011/154767 | 12/2011 |
| WO | WO 2012/014018 | 2/2012 |

OTHER PUBLICATIONS

European Search Report dated Jul. 26, 2012 in copending European Appln. No. 12165851.

(Continued)

*Primary Examiner* — Theodore Stigell
*Assistant Examiner* — Benjamin Koo
(74) *Attorney, Agent, or Firm* — Lisa E. Winsor, Esq.

(57) ABSTRACT

A safety intravenous (IV) catheter assembly is disclosed which includes a safety device having a housing defining a cavity and distal and proximal openings, and a biasing member positioned within the cavity. The biasing member is movable from a first position to a second position to tilt the housing in relation to the needle when the needle tip is withdrawn through the distal opening of the housing to misalign the needle tip and the distal opening. A blocking arm is provided on the biasing member to prevent the biasing member from moving from the second position back to the first position.

21 Claims, 27 Drawing Sheets

(56) References Cited

U.S. PATENT DOCUMENTS

| | | |
|---|---|---|
| 4,795,432 A | 1/1989 | Karczmer |
| 4,804,370 A | 2/1989 | Haber |
| 4,804,371 A | 2/1989 | Vaillancourt |
| 4,808,169 A | 2/1989 | Haber |
| 4,834,718 A | 5/1989 | Mc donald |
| 4,842,591 A | 6/1989 | Luther |
| 4,846,805 A | 7/1989 | Sitar |
| 4,850,977 A | 7/1989 | Bayless |
| 4,850,994 A | 7/1989 | Zerbst |
| 4,863,434 A | 9/1989 | Bayless |
| 4,863,436 A | 9/1989 | Glick |
| 4,867,746 A | 9/1989 | Dufresne |
| 4,874,377 A | 10/1989 | Newgard |
| 4,908,022 A | 3/1990 | Haber |
| 4,909,794 A | 3/1990 | Haber |
| 4,911,706 A | 3/1990 | Levitt |
| 4,917,668 A | 4/1990 | Haindl |
| 4,921,486 A | 5/1990 | De chellis |
| 4,921,490 A | 5/1990 | Spier |
| 4,927,415 A | 5/1990 | Brodsky |
| 4,929,241 A | 5/1990 | Kulli |
| 4,931,040 A | 6/1990 | Haber |
| 4,935,010 A | 6/1990 | Cox |
| 4,944,723 A | 7/1990 | Haber |
| 4,944,728 A | 7/1990 | Carrell |
| 4,952,207 A | 8/1990 | Lemieux |
| 4,955,866 A | 9/1990 | Corey |
| 4,964,854 A | 10/1990 | Luther |
| 4,978,343 A | 12/1990 | Dysarz |
| 4,978,344 A | 12/1990 | Dombrowski |
| 4,986,813 A | 1/1991 | Blake, III |
| 4,986,819 A | 1/1991 | Sobel |
| 4,994,041 A | 2/1991 | Dombrowski |
| 4,994,046 A | 2/1991 | Wesson |
| 4,998,922 A | 3/1991 | Kuracina |
| 5,002,533 A | 3/1991 | Jullien |
| 5,013,305 A | 5/1991 | Opie |
| 5,015,234 A | 5/1991 | Jullien |
| 5,015,240 A | 5/1991 | Soproni |
| 5,015,241 A | 5/1991 | Feimer |
| 5,015,242 A | 5/1991 | Heifetz |
| 5,030,208 A | 7/1991 | Novacek |
| 5,049,136 A | 9/1991 | Johnson |
| 5,051,109 A | 9/1991 | Simon |
| 5,053,014 A | 10/1991 | Van heugten |
| 5,053,017 A | 10/1991 | Chamuel |
| 5,059,180 A | 10/1991 | Mclees |
| 5,059,184 A | 10/1991 | Dyke |
| 5,080,651 A | 1/1992 | Julien |
| 5,084,018 A | 1/1992 | Tsao |
| 5,085,648 A | 2/1992 | Purdy |
| 5,092,461 A | 3/1992 | Adam |
| 5,092,851 A | 3/1992 | Ragner |
| 5,104,378 A | 4/1992 | Haber |
| 5,112,311 A | 5/1992 | Utterberg |
| 5,114,404 A | 5/1992 | Paxton |
| 5,120,321 A | 6/1992 | Oksman |
| 5,122,118 A | 6/1992 | Haber |
| 5,122,124 A | 6/1992 | Novacek |
| 5,127,905 A | 7/1992 | Lemieux |
| 5,131,405 A | 7/1992 | Burns |
| 5,135,504 A | 8/1992 | Mc lees |
| 5,137,515 A | 8/1992 | Hogan |
| 5,147,327 A | 9/1992 | Johnson |
| 5,154,699 A | 10/1992 | Ryan |
| 5,154,703 A | 10/1992 | Bonaldo |
| 5,156,596 A | 10/1992 | Balbierz |
| 5,158,554 A | 10/1992 | Jepson |
| 5,169,391 A | 12/1992 | Vogel |
| 5,171,229 A | 12/1992 | Mc neil |
| 5,171,300 A | 12/1992 | Blake, III |
| 5,176,650 A | 1/1993 | Haining |
| 5,176,655 A | 1/1993 | Mc cormick |
| 5,176,656 A | 1/1993 | Bayless |
| 5,180,369 A | 1/1993 | Dysarz |
| 5,180,370 A | 1/1993 | Gillespie |
| 5,183,468 A | 2/1993 | Mclees |
| 5,188,607 A | 2/1993 | Wu |
| 5,195,723 A | 3/1993 | Schauerte |
| 5,195,974 A | 3/1993 | Hardy |
| 5,195,980 A | 3/1993 | Catlin |
| 5,199,947 A | 4/1993 | Lopez |
| 5,205,827 A | 4/1993 | Novacek |
| 5,205,829 A | 4/1993 | Lituchy |
| 5,207,656 A | 5/1993 | Kranys |
| 5,211,629 A | 5/1993 | Pressly |
| 5,211,633 A | 5/1993 | Stouder, Jr. |
| 5,215,525 A | 6/1993 | Sturman |
| 5,215,528 A | 6/1993 | Purdy |
| 5,215,533 A | 6/1993 | Robb |
| 5,215,534 A | 6/1993 | De harde |
| 5,215,538 A | 6/1993 | Larkin |
| 5,222,505 A | 6/1993 | Burns |
| 5,224,936 A | 7/1993 | Gallagher |
| 5,228,646 A | 7/1993 | Raines |
| 5,232,456 A | 8/1993 | Gonzalez |
| 5,232,458 A | 8/1993 | Chen |
| 5,234,410 A | 8/1993 | Graham |
| 5,242,393 A | 9/1993 | Brimball |
| 5,242,400 A | 9/1993 | Blake, III |
| 5,242,402 A | 9/1993 | Chen |
| 5,242,411 A | 9/1993 | Yamamoto |
| 5,246,427 A | 9/1993 | Sturman |
| RE34,416 E | 10/1993 | Lemieux |
| 5,251,873 A | 10/1993 | Atkinson |
| 5,254,099 A | 10/1993 | Kuracina |
| 5,256,152 A | 10/1993 | Marks |
| 5,261,880 A | 11/1993 | Streck |
| 5,261,894 A | 11/1993 | Smith |
| 5,263,933 A | 11/1993 | Novacek |
| 5,266,072 A | 11/1993 | Utterberg |
| 5,267,966 A | 12/1993 | Paul |
| 5,267,976 A | 12/1993 | Guerineau |
| 5,269,763 A | 12/1993 | Boehmer |
| 5,269,764 A | 12/1993 | Vetter |
| 5,269,765 A | 12/1993 | Kuracina |
| 5,269,771 A | 12/1993 | Thomas |
| 5,273,540 A | 12/1993 | Luther |
| 5,277,342 A | 1/1994 | Dickau |
| 5,279,570 A | 1/1994 | Dombrowski |
| 5,279,571 A | 1/1994 | Larkin |
| 5,279,591 A | 1/1994 | Simon |
| 5,290,246 A | 3/1994 | Yamamoto |
| 5,293,970 A | 3/1994 | Schneider |
| 5,295,657 A | 3/1994 | Atkinson |
| 5,295,658 A | 3/1994 | Atkinson |
| 5,295,963 A | 3/1994 | Deeks |
| 5,295,972 A | 3/1994 | Mischenko |
| 5,297,777 A | 3/1994 | Yie |
| 5,300,032 A | 4/1994 | Hibbs |
| 5,300,033 A | 4/1994 | Miller |
| 5,300,034 A | 4/1994 | Behnke |
| 5,300,035 A | 4/1994 | Clement |
| 5,300,040 A | 4/1994 | Martin |
| 5,300,045 A | 4/1994 | Plassche, Jr. |
| 5,304,136 A | 4/1994 | Erskine |
| 5,304,151 A | 4/1994 | Kuracina |
| 5,304,156 A | 4/1994 | Sylvanowicz |
| 5,306,243 A | 4/1994 | Bonaldo |
| 5,308,336 A | 5/1994 | Hart |
| 5,312,355 A | 5/1994 | Lee |
| 5,312,362 A | 5/1994 | Pfolsgraf |
| 5,312,363 A | 5/1994 | Ryan |
| 5,312,371 A | 5/1994 | Dombrowski |
| 5,312,372 A | 5/1994 | De harde |
| 5,322,517 A | 6/1994 | Sircom |
| 5,322,518 A | 6/1994 | Schneider |
| 5,324,271 A | 6/1994 | Abiuso |
| 5,328,478 A | 7/1994 | Mcvay |
| 5,328,482 A | 7/1994 | Sircom |
| 5,328,484 A | 7/1994 | Somers |
| 5,328,485 A | 7/1994 | Moreno |
| 5,330,435 A | 7/1994 | Vaillancourt |
| 5,330,437 A | 7/1994 | Durman |

(56) References Cited

U.S. PATENT DOCUMENTS

| | | |
|---|---|---|
| 5,334,158 A | 8/1994 | Mc lees |
| 5,334,159 A | 8/1994 | Turkel |
| 5,336,192 A | 8/1994 | Palestrant |
| 5,336,198 A | 8/1994 | Silver |
| 5,336,199 A | 8/1994 | Castillo |
| 5,336,200 A | 8/1994 | Streck |
| 5,342,316 A | 8/1994 | Wallace |
| 5,342,319 A | 8/1994 | Watson |
| 5,344,161 A | 9/1994 | Sandgren |
| 5,344,408 A | 9/1994 | Partika |
| 5,344,414 A | 9/1994 | Lopez |
| 5,348,544 A | 9/1994 | Sweeney |
| 5,350,362 A | 9/1994 | Stouder, Jr. |
| 5,350,363 A | 9/1994 | Goode |
| 5,352,205 A | 10/1994 | Dales |
| 5,353,837 A | 10/1994 | Faust |
| 5,354,280 A | 10/1994 | Haber |
| 5,356,384 A | 10/1994 | Haber |
| 5,360,413 A | 11/1994 | Leason |
| 5,364,370 A | 11/1994 | Szerlip |
| 5,364,372 A | 11/1994 | Danks |
| 5,368,574 A | 11/1994 | Antonacci |
| 5,376,077 A | 12/1994 | Gomringer |
| 5,380,288 A | 1/1995 | Hart |
| 5,380,305 A | 1/1995 | Ghouri |
| 5,382,235 A | 1/1995 | Sak |
| 5,383,860 A | 1/1995 | Lau |
| 5,385,550 A | 1/1995 | Su |
| 5,389,081 A | 2/1995 | Castro |
| 5,390,898 A | 2/1995 | Smedley |
| 5,395,338 A | 3/1995 | Gaba |
| 5,395,346 A | 3/1995 | Maggioni |
| 5,395,347 A | 3/1995 | Blecher |
| 5,395,352 A | 3/1995 | Penny |
| 5,403,284 A | 4/1995 | Gross |
| 5,405,323 A | 4/1995 | Rogers |
| 5,405,327 A | 4/1995 | Chen |
| 5,405,331 A | 4/1995 | Behnke |
| 5,409,461 A | 4/1995 | Steinman |
| 5,409,464 A | 4/1995 | Villalobos |
| 5,411,486 A | 5/1995 | Zadini |
| 5,411,492 A | 5/1995 | Sturman |
| 5,415,638 A | 5/1995 | Novacek |
| 5,417,659 A | 5/1995 | Gaba |
| 5,417,673 A | 5/1995 | Gordon |
| 5,419,766 A | 5/1995 | Chang |
| 5,423,766 A | 6/1995 | Cesare |
| 5,425,718 A | 6/1995 | Tay |
| 5,425,720 A | 6/1995 | Rogalsky |
| 5,429,596 A | 7/1995 | Arias |
| 5,429,619 A | 7/1995 | Furnish |
| 5,431,631 A | 7/1995 | Lu |
| 5,431,632 A | 7/1995 | Lu |
| 5,433,703 A | 7/1995 | Utterberg |
| 5,437,646 A | 8/1995 | Hunt |
| 5,439,451 A | 8/1995 | Collinson |
| 5,441,487 A | 8/1995 | Vedder |
| 5,443,452 A | 8/1995 | Hart |
| 5,443,454 A | 8/1995 | Tanabe |
| 5,447,501 A | 9/1995 | Karlsson |
| 5,453,095 A | 9/1995 | Davila |
| 5,454,790 A | 10/1995 | Dubrul |
| 5,456,284 A | 10/1995 | Ryan |
| 5,456,675 A | 10/1995 | Wolbring |
| 5,458,640 A | 10/1995 | Gerrone |
| 5,458,658 A | 10/1995 | Sircom |
| 5,460,603 A | 10/1995 | Desantis |
| 5,462,531 A | 10/1995 | Novacek |
| 5,465,938 A | 11/1995 | Werge |
| 5,466,223 A | 11/1995 | Bressler |
| 5,466,230 A | 11/1995 | Davila |
| 5,470,319 A | 11/1995 | Mayer |
| 5,472,418 A | 12/1995 | Palestrant |
| 5,474,544 A | 12/1995 | Lynn |
| 5,478,313 A | 12/1995 | White |
| 5,480,393 A | 1/1996 | Bommarito |
| 5,484,401 A | 1/1996 | Rodriguez |
| 5,486,190 A | 1/1996 | Green |
| 5,487,728 A | 1/1996 | Vaillancourt |
| 5,487,733 A | 1/1996 | Caizza |
| 5,487,850 A | 1/1996 | Vanderploeg |
| 5,489,274 A | 2/1996 | Chu |
| 5,492,147 A | 2/1996 | Challender |
| 5,492,304 A | 2/1996 | Smith |
| 5,496,274 A | 3/1996 | Graves |
| 5,496,280 A | 3/1996 | Vandenbroek |
| 5,501,426 A | 3/1996 | Atkinson |
| 5,501,670 A | 3/1996 | Sak |
| 5,501,675 A | 3/1996 | Erskine |
| 5,507,732 A | 4/1996 | Mcclure |
| 5,509,433 A | 4/1996 | Paradis |
| 5,514,098 A | 5/1996 | Pfolsgraf |
| 5,514,116 A | 5/1996 | Vaillancourt |
| 5,514,117 A | 5/1996 | Lynn |
| 5,520,649 A | 5/1996 | Novacek |
| 5,520,655 A | 5/1996 | Davila |
| 5,520,666 A | 5/1996 | Choudhury |
| 5,531,701 A | 7/1996 | Luther |
| 5,533,974 A | 7/1996 | Gaba |
| 5,533,975 A | 7/1996 | Lu |
| 5,535,785 A | 7/1996 | Werge |
| 5,538,505 A | 7/1996 | Weinstein |
| 5,538,508 A | 7/1996 | Steyn |
| 5,540,661 A | 7/1996 | Tomisaka |
| 5,540,662 A | 7/1996 | Nicholson |
| 5,545,146 A | 8/1996 | Ishak |
| 5,545,152 A | 8/1996 | Funderburk |
| 5,549,565 A | 8/1996 | Ryan |
| 5,549,566 A | 8/1996 | Elias |
| 5,549,570 A | 8/1996 | Rogalsky |
| 5,549,576 A | 8/1996 | Patterson |
| 5,549,651 A | 8/1996 | Lynn |
| 5,554,131 A | 9/1996 | Lacivita |
| 5,558,651 A | 9/1996 | Crawford |
| 5,562,629 A | 10/1996 | Haughton |
| 5,562,630 A | 10/1996 | Nichols |
| 5,562,632 A | 10/1996 | Davila |
| 5,562,633 A | 10/1996 | Wozencroft |
| 5,562,636 A | 10/1996 | Utterberg |
| 5,562,637 A | 10/1996 | Utterberg |
| 5,569,202 A | 10/1996 | Kovalic |
| 5,569,203 A | 10/1996 | Chen |
| 5,569,205 A | 10/1996 | Hart |
| 5,569,209 A | 10/1996 | Roitman |
| 5,569,288 A | 10/1996 | Yoon |
| 5,573,545 A | 11/1996 | Yoon |
| 5,575,774 A | 11/1996 | Chen |
| 5,575,777 A | 11/1996 | Davidner |
| 5,575,804 A | 11/1996 | Yoon |
| 5,578,059 A | 11/1996 | Patzer |
| 5,582,594 A | 12/1996 | Chen |
| 5,582,597 A | 12/1996 | Brimhall |
| 5,584,808 A | 12/1996 | Healy |
| 5,584,809 A | 12/1996 | Gaba |
| 5,584,810 A * | 12/1996 | Brimhall ..................... 604/110 |
| 5,584,818 A | 12/1996 | Morrison |
| 5,584,848 A | 12/1996 | Yoon |
| 5,584,849 A | 12/1996 | Yoon |
| 5,584,850 A | 12/1996 | Hart |
| 5,588,966 A | 12/1996 | Atsumi |
| 5,591,134 A | 1/1997 | Shu |
| 5,591,137 A | 1/1997 | Stevens |
| 5,591,190 A | 1/1997 | Yoon |
| 5,591,193 A | 1/1997 | Yoon |
| 5,599,310 A | 2/1997 | Bogert |
| 5,601,532 A | 2/1997 | Gaba |
| 5,601,534 A | 2/1997 | Turner |
| 5,601,536 A | 2/1997 | Crawford |
| 5,607,396 A | 3/1997 | Yoon |
| 5,607,439 A | 3/1997 | Yoon |
| 5,611,781 A | 3/1997 | Sircom |
| 5,611,792 A | 3/1997 | Gustafsson |
| 5,613,500 A | 3/1997 | Bishop |
| 5,613,663 A | 3/1997 | Schmidt |

(56) References Cited

U.S. PATENT DOCUMENTS

| | | |
|---|---|---|
| 5,613,952 A | 3/1997 | Pressly, Sr. |
| 5,613,954 A | 3/1997 | Nelson |
| 5,613,956 A | 3/1997 | Patterson |
| 5,616,129 A | 4/1997 | Mayer |
| 5,616,130 A | 4/1997 | Mayer |
| 5,618,271 A | 4/1997 | Yoon |
| 5,630,803 A | 5/1997 | Tamaro |
| 5,634,913 A | 6/1997 | Stinger |
| 5,634,934 A | 6/1997 | Yoon |
| 5,643,227 A | 7/1997 | Stevens |
| 5,645,076 A | 7/1997 | Yoon |
| 5,645,533 A | 7/1997 | Blaeser |
| 5,651,772 A | 7/1997 | Arnett |
| 5,653,698 A | 8/1997 | Niedospial |
| 5,662,610 A | 9/1997 | Sircom |
| 5,669,891 A | 9/1997 | Vaillancourt |
| 5,672,160 A | 9/1997 | Osterlind |
| 5,672,161 A | 9/1997 | Allen |
| 5,676,681 A | 10/1997 | Yoon |
| 5,676,682 A | 10/1997 | Yoon |
| 5,676,683 A | 10/1997 | Yoon |
| 5,683,365 A | 11/1997 | Brown |
| 5,683,368 A | 11/1997 | Schmidt |
| 5,685,855 A | 11/1997 | Erskine |
| 5,685,860 A | 11/1997 | Chang |
| 5,688,240 A | 11/1997 | Novacek |
| 5,688,253 A | 11/1997 | Paradis |
| 5,688,254 A | 11/1997 | Lopez |
| 5,688,286 A | 11/1997 | Yoon |
| 5,693,025 A | 12/1997 | Stevens |
| 5,693,031 A | 12/1997 | Ryan |
| 5,695,474 A | 12/1997 | Daugherty |
| 5,696,466 A | 12/1997 | Li |
| 5,697,907 A | 12/1997 | Gaba |
| 5,699,821 A | 12/1997 | Paradis |
| 5,700,249 A | 12/1997 | Jenkins |
| 5,700,250 A | 12/1997 | Erskine |
| 5,702,367 A | 12/1997 | Cover |
| 5,709,664 A | 1/1998 | Vandenbroek |
| 5,718,688 A | 2/1998 | Wozencroft |
| 5,718,689 A | 2/1998 | Stevenson |
| 5,718,691 A | 2/1998 | Russo |
| 5,720,734 A | 2/1998 | Copenhaver |
| 5,722,958 A | 3/1998 | Gravener |
| 5,725,503 A | 3/1998 | Arnett |
| 5,735,827 A | 4/1998 | Adwers |
| 5,738,144 A | 4/1998 | Rogers |
| 5,738,665 A | 4/1998 | Caizza |
| 5,743,884 A | 4/1998 | Hasson |
| 5,743,888 A | 4/1998 | Wilkes |
| 5,743,891 A | 4/1998 | Tolkoff et al. |
| 5,746,718 A | 5/1998 | Steyn |
| 5,749,857 A | 5/1998 | Cuppy |
| 5,749,859 A | 5/1998 | Powell |
| 5,749,861 A | 5/1998 | Guala |
| 5,749,889 A | 5/1998 | Bacich |
| 5,755,699 A | 5/1998 | Blecher |
| 5,755,701 A | 5/1998 | Sarstedt |
| 5,772,636 A | 6/1998 | Brimhall |
| 5,776,113 A | 7/1998 | Daugherty |
| 5,779,681 A | 7/1998 | Bonn |
| 5,779,684 A | 7/1998 | Tamaro |
| 5,782,804 A | 7/1998 | Mcmahon |
| D397,434 S | 8/1998 | Pike |
| 5,788,675 A | 8/1998 | Mayer |
| 5,792,121 A | 8/1998 | Tamaro |
| 5,795,339 A | 8/1998 | Erskine |
| 5,797,897 A | 8/1998 | Jepson |
| 5,800,403 A | 9/1998 | Pressly, Sr. |
| 5,803,919 A | 9/1998 | Hart |
| 5,806,831 A | 9/1998 | Paradis |
| 5,807,350 A | 9/1998 | Diaz |
| 5,807,352 A | 9/1998 | Tamaro |
| 5,807,353 A | 9/1998 | Schmitz |
| 5,810,784 A | 9/1998 | Tamaro |
| 5,814,018 A | 9/1998 | Elson |
| 5,817,069 A | 10/1998 | Arnett |
| 5,817,070 A | 10/1998 | Tamaro |
| 5,820,606 A | 10/1998 | Davis |
| 5,820,614 A | 10/1998 | Erskine |
| 5,820,621 A | 10/1998 | Yale |
| 5,830,189 A | 11/1998 | Chang |
| 5,833,670 A | 11/1998 | Dillon |
| 5,851,196 A | 12/1998 | Arnett |
| 5,853,393 A | 12/1998 | Bogert |
| 5,853,399 A | 12/1998 | Sasaki |
| 5,857,999 A | 1/1999 | Quick |
| 5,858,000 A | 1/1999 | Novacek |
| 5,858,007 A | 1/1999 | Fagan |
| 5,865,806 A | 2/1999 | Howell |
| 5,871,471 A | 2/1999 | Ryan |
| 5,879,331 A | 3/1999 | Osterlind |
| 5,879,337 A | 3/1999 | Kuracina |
| 5,882,337 A | 3/1999 | Bogert |
| 5,885,256 A | 3/1999 | Chern et al. |
| 5,891,093 A | 4/1999 | Dysarz |
| 5,899,887 A | 5/1999 | Liu |
| 5,910,130 A | 6/1999 | Caizza |
| 5,911,705 A | 6/1999 | Howell |
| 5,911,710 A | 6/1999 | Barry |
| 5,916,198 A | 6/1999 | Dillow |
| 5,919,168 A | 7/1999 | Wheeler |
| 5,919,174 A | 7/1999 | Hanson |
| 5,925,020 A | 7/1999 | Nestell |
| 5,935,104 A | 8/1999 | Janek |
| 5,941,850 A | 8/1999 | Shah |
| 5,951,515 A | 9/1999 | Osterlind |
| 5,951,529 A | 9/1999 | Utterberg |
| 5,954,698 A | 9/1999 | Pike |
| 5,954,708 A | 9/1999 | Lopez |
| 5,957,887 A | 9/1999 | Osterlind |
| 5,957,898 A | 9/1999 | Jepson |
| 5,967,490 A | 10/1999 | Pike |
| 5,968,068 A | 10/1999 | Dehdashtian |
| 5,971,957 A | 10/1999 | Luther |
| 5,989,224 A | 11/1999 | Exline |
| 5,993,419 A | 11/1999 | Lo |
| 5,997,486 A | 12/1999 | Burek |
| 5,997,507 A | 12/1999 | Dysarz |
| 6,001,080 A | 12/1999 | Kuracina |
| 6,004,294 A | 12/1999 | Brimhall |
| 6,012,213 A | 1/2000 | Chang |
| 6,015,397 A | 1/2000 | Elson |
| 6,024,729 A | 2/2000 | Dehdashtian |
| 6,033,386 A | 3/2000 | Novacek |
| 6,036,672 A | 3/2000 | Allen |
| 6,039,302 A | 3/2000 | Cote, Sr. |
| 6,048,335 A | 4/2000 | Mayer |
| 6,053,861 A | 4/2000 | Grossi |
| 6,068,011 A | 5/2000 | Paradis |
| 6,074,370 A | 6/2000 | Pressly, Jr. |
| 6,077,244 A | 6/2000 | Botich |
| 6,079,432 A | 6/2000 | Paradis |
| 6,080,135 A | 6/2000 | Van Stokkum |
| 6,080,137 A | 6/2000 | Pike |
| 6,086,566 A | 7/2000 | Arnissolle |
| 6,099,500 A | 8/2000 | Dysarz |
| 6,099,505 A | 8/2000 | Ryan |
| 6,102,894 A | 8/2000 | Dysarz |
| RE36,885 E | 9/2000 | Blecher |
| 6,117,107 A | 9/2000 | Chen |
| 6,117,108 A | 9/2000 | Woehr |
| 6,117,110 A | 9/2000 | Radmand |
| 6,117,113 A | 9/2000 | Novacek |
| 6,127,320 A | 10/2000 | Ooij |
| 6,152,900 A | 11/2000 | Mayer |
| 6,156,010 A | 12/2000 | Kuracina |
| 6,159,185 A | 12/2000 | Tanihata |
| 6,162,196 A | 12/2000 | Hart |
| 6,171,287 B1 | 1/2001 | Lynn |
| 6,183,440 B1 | 2/2001 | Bell |
| 6,183,448 B1 | 2/2001 | Mayer |
| 6,193,690 B1 | 2/2001 | Dysarz |
| 6,200,262 B1 | 3/2001 | Ouchi |

(56) References Cited

U.S. PATENT DOCUMENTS

| | | |
|---|---|---|
| 6,203,527 B1 | 3/2001 | Zadini |
| 6,203,533 B1 | 3/2001 | Ouchi |
| 6,206,857 B1 | 3/2001 | Chen |
| 6,210,373 B1 | 4/2001 | Allmon |
| 6,213,978 B1 | 4/2001 | Voyten |
| 6,217,555 B1 | 4/2001 | Hart |
| 6,217,568 B1 | 4/2001 | Jepson |
| 6,221,047 B1 | 4/2001 | Greene |
| 6,221,050 B1 | 4/2001 | Ishida |
| 6,221,056 B1 | 4/2001 | Silverman |
| 6,224,569 B1 | 5/2001 | Brimhall |
| 6,228,060 B1 | 5/2001 | Howell |
| 6,234,999 B1 | 5/2001 | Wemmert |
| 6,235,003 B1 | 5/2001 | Dysarz |
| 6,235,006 B1 | 5/2001 | Dillon |
| 6,241,707 B1 | 6/2001 | Dysarz |
| 6,245,045 B1 | 6/2001 | Stratienko |
| 6,245,048 B1 | 6/2001 | Fangrow |
| 6,254,529 B1 | 7/2001 | Ouchi |
| 6,258,065 B1 | 7/2001 | Dennis |
| 6,261,264 B1 | 7/2001 | Tamaro |
| 6,261,265 B1 | 7/2001 | Mosseri |
| 6,273,869 B1 | 8/2001 | Vaillancourt |
| 6,277,100 B1 | 8/2001 | Raulerson |
| 6,280,419 B1 | 8/2001 | Vojtasek |
| 6,287,278 B1 | 9/2001 | Woehr |
| 6,287,279 B1 | 9/2001 | Siekmann |
| 6,287,280 B1 | 9/2001 | Lampropoulos |
| 6,306,124 B1 | 10/2001 | Jones |
| 6,322,537 B1 | 11/2001 | Chang |
| 6,322,541 B2 | 11/2001 | West |
| 6,342,045 B1 | 1/2002 | Somers |
| 6,344,031 B1 | 2/2002 | Novacek |
| 6,344,033 B1 | 2/2002 | Jepson |
| 6,352,520 B1 | 3/2002 | Miyazaki |
| 6,352,521 B1 | 3/2002 | Prosl |
| 6,358,265 B1 | 3/2002 | Thorne, Jr. |
| 6,379,332 B1 | 4/2002 | Van Landuyt |
| 6,379,333 B1 | 4/2002 | Brimhall |
| 6,379,372 B1 | 4/2002 | Dehdashtian |
| 6,394,983 B1 | 5/2002 | Mayoral |
| 6,402,721 B1 | 6/2002 | Lo |
| 6,406,459 B1 | 6/2002 | Allmon |
| 6,409,703 B1 | 6/2002 | Lu |
| 6,413,236 B1 | 7/2002 | Van Dyke |
| 6,416,499 B2 | 7/2002 | Paul, Jr. |
| 6,425,884 B1 | 7/2002 | Wemmert |
| 6,440,101 B1 | 8/2002 | Grabenkort |
| 6,443,927 B1 | 9/2002 | Cook |
| 6,443,929 B1 | 9/2002 | Kuracina |
| 6,461,328 B2 | 10/2002 | Wang |
| 6,475,194 B2 | 11/2002 | Domici, Jr. |
| 6,485,459 B1 | 11/2002 | Surowitz |
| 6,485,468 B2 | 11/2002 | Vojtasek |
| 6,488,656 B1 | 12/2002 | Wu |
| 6,488,663 B1 | 12/2002 | Steg |
| 6,488,674 B2 | 12/2002 | Becker |
| 6,506,181 B2 | 1/2003 | Meng |
| 6,520,939 B2 | 2/2003 | Lafontaine |
| 6,524,276 B1 | 2/2003 | Halseth |
| 6,524,278 B1 | 2/2003 | Campbell |
| 6,527,747 B2 | 3/2003 | Adams |
| 6,530,903 B2 | 3/2003 | Wang |
| 6,533,759 B1 | 3/2003 | Watson |
| 6,537,259 B1 | 3/2003 | Niermann |
| 6,545,242 B1 | 4/2003 | Butler |
| 6,551,283 B1 | 4/2003 | Guo |
| 6,569,119 B1 | 5/2003 | Haberland |
| 6,572,591 B2 | 6/2003 | Mayer |
| 6,582,402 B1 | 6/2003 | Erskine |
| 6,585,701 B1 | 7/2003 | Dysarz |
| 6,585,704 B2 | 7/2003 | Luther |
| 6,592,555 B1 | 7/2003 | Pi |
| 6,592,556 B1 | 7/2003 | Thorne |
| 6,595,954 B1 | 7/2003 | Luther |
| 6,595,955 B2 | 7/2003 | Ferguson |
| 6,595,964 B2 | 7/2003 | Finley |
| 6,595,965 B1 | 7/2003 | Utterberg |
| 6,595,981 B2 | 7/2003 | Huet |
| 6,602,240 B2 | 8/2003 | Hermann |
| 6,605,073 B1 | 8/2003 | Pressly, Sr. |
| 6,610,031 B1 | 8/2003 | Chin |
| 6,616,630 B1 | 9/2003 | Woehr |
| 6,616,640 B2 | 9/2003 | Chen |
| 6,620,136 B1 | 9/2003 | Pressly, Sr. |
| 6,623,458 B2 | 9/2003 | Woehr |
| 6,629,959 B2 | 10/2003 | Kuracina |
| 6,632,200 B2 | 10/2003 | Guo |
| 6,632,201 B1 | 10/2003 | Mathias |
| 6,641,564 B1 | 11/2003 | Kraus |
| 6,651,956 B2 | 11/2003 | Miller |
| 6,652,486 B2 | 11/2003 | Bialecki |
| 6,652,490 B2 | 11/2003 | Howell |
| 6,663,592 B2 | 12/2003 | Rhad |
| 6,663,599 B2 | 12/2003 | Osborne |
| 6,669,666 B2 | 12/2003 | Lu |
| 6,669,681 B2 | 12/2003 | Jepson |
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,706,022 B1 | 3/2004 | Leinsing |
| 6,709,419 B2 | 3/2004 | Woehr |
| 6,712,791 B2 | 3/2004 | Lui |
| 6,719,726 B2 | 4/2004 | Meng |
| 6,723,073 B2 | 4/2004 | Ley |
| 6,736,798 B2 | 5/2004 | Ohkubo |
| 6,743,199 B2 | 6/2004 | Shue |
| 6,749,588 B1 | 6/2004 | Howell |
| 6,761,704 B2 | 7/2004 | Crawford |
| 6,761,705 B1 | 7/2004 | Chiu |
| 6,761,706 B2 | 7/2004 | Vaillancourt |
| 6,764,468 B1 | 7/2004 | East |
| 6,767,340 B2 | 7/2004 | Willis |
| 6,770,059 B1 | 8/2004 | Spinks |
| 6,773,416 B1 | 8/2004 | Hsu |
| 6,776,774 B2 | 8/2004 | Tansey, Jr. |
| 6,796,962 B2 | 9/2004 | Ferguson |
| 6,796,968 B2 | 9/2004 | Ferguson |
| 6,796,969 B1 | 9/2004 | Andersson |
| 6,802,827 B2 | 10/2004 | Andersson |
| 6,808,161 B1 | 10/2004 | Hishikawa |
| 6,808,509 B1 | 10/2004 | Davey |
| 6,811,545 B2 | 11/2004 | Vaillancourt |
| 6,817,989 B2 | 11/2004 | Svendsen |
| 6,821,266 B2 | 11/2004 | Knepshield |
| 6,824,527 B2 | 11/2004 | Gollobin |
| 6,832,992 B2 | 12/2004 | Wilkinson |
| 6,855,127 B2 | 2/2005 | Nakagami |
| 6,855,130 B2 | 2/2005 | Saulenas |
| 6,860,869 B2 | 3/2005 | Dennis |
| 6,860,871 B2 | 3/2005 | Kuracina |
| 6,863,659 B2 | 3/2005 | Sharpe |
| 6,866,656 B2 | 3/2005 | Tingey |
| 6,878,131 B2 | 4/2005 | Novacek |
| 6,878,134 B2 | 4/2005 | Rogers |
| 6,883,778 B1 | 4/2005 | Newton |
| 6,884,224 B2 | 4/2005 | Dalton |
| 6,886,808 B2 | 5/2005 | Sarno |
| 6,893,423 B2 | 5/2005 | Denolly |
| 6,902,546 B2 | 6/2005 | Ferguson |
| 6,905,483 B2 | 6/2005 | Newby |
| 6,908,459 B2 | 6/2005 | Harding |
| 6,911,018 B2 | 6/2005 | Gordon |
| 6,913,595 B2 | 7/2005 | Mastorakis |
| 6,916,309 B2 | 7/2005 | Fangrow, Jr. |
| 6,916,311 B2 | 7/2005 | Vojtasek |
| 6,918,891 B2 | 7/2005 | Bressler |
| 6,921,382 B2 | 7/2005 | Lee |
| 6,921,386 B2 | 7/2005 | Shue |
| 6,926,698 B2 | 8/2005 | Lin |
| 6,926,700 B2 | 8/2005 | Bressler |

(56) References Cited

U.S. PATENT DOCUMENTS

| | | |
|---|---|---|
| 6,929,622 B2 | 8/2005 | Chian |
| 6,932,803 B2 | 8/2005 | Newby |
| 6,936,031 B2 | 8/2005 | Caleffi |
| 6,936,036 B2 | 8/2005 | Wilkinson |
| 6,942,642 B2 | 9/2005 | Suzuki |
| 6,958,055 B2 | 10/2005 | Donnan |
| 6,972,002 B2 | 12/2005 | Thorne |
| 6,979,314 B2 | 12/2005 | Hsieh |
| 6,981,965 B2 | 1/2006 | Luther |
| 6,984,213 B2 | 1/2006 | Horner |
| 6,986,759 B1 | 1/2006 | Jeremijevic |
| 6,991,215 B2 | 1/2006 | Kiehne |
| RE38,996 E | 2/2006 | Crawford |
| 6,997,902 B2 | 2/2006 | Thorne |
| 7,004,927 B2 | 2/2006 | Ferguson |
| 7,004,934 B2 | 2/2006 | Vaillancourt |
| 7,008,402 B2 | 3/2006 | Ferguson |
| 7,008,404 B2 | 3/2006 | Nakajima |
| 7,014,623 B2 | 3/2006 | Prestidge |
| 7,018,344 B2 | 3/2006 | Bressler |
| 7,018,365 B2 | 3/2006 | Strauss |
| 7,025,721 B2 | 4/2006 | Cohen |
| 7,025,744 B2 | 4/2006 | Utterberg |
| 7,033,339 B1 | 4/2006 | Lynn |
| 7,033,345 B2 | 4/2006 | Lee |
| 7,037,292 B2 | 5/2006 | Carlyon |
| 7,037,303 B2 | 5/2006 | Beaufore |
| 7,060,053 B2 | 6/2006 | Nakashima |
| 7,063,685 B2 | 6/2006 | Rome |
| 7,066,908 B2 | 6/2006 | Kuracina |
| 7,077,824 B2 | 7/2006 | Meyer |
| 7,081,106 B1 | 7/2006 | Guo |
| 7,083,596 B2 | 8/2006 | Saied |
| 7,083,600 B2 | 8/2006 | Meloul |
| 7,101,351 B2 | 9/2006 | Crawford |
| 7,101,353 B2 | 9/2006 | Lui |
| 7,104,970 B2 | 9/2006 | Chen |
| 7,112,191 B2 | 9/2006 | Daga |
| 7,125,396 B2 | 10/2006 | Leinsing |
| 7,125,397 B2 | 10/2006 | Woehr |
| 7,147,621 B2 | 12/2006 | Kiehne |
| 7,150,725 B2 | 12/2006 | Wilkinson |
| 7,160,269 B2 | 1/2007 | Woehr |
| 7,172,580 B2 | 2/2007 | Hruska |
| 7,175,610 B2 | 2/2007 | Mori |
| 7,179,244 B2 | 2/2007 | Smith |
| 7,182,734 B2 | 2/2007 | Saulenas |
| 7,186,239 B2 | 3/2007 | Woehr |
| 7,192,433 B2 | 3/2007 | Osypka |
| 7,198,618 B2 | 4/2007 | Ferguson |
| 7,207,975 B2 | 4/2007 | Miller |
| 7,214,208 B2 | 5/2007 | Vaillancourt |
| 7,214,211 B2 | 5/2007 | Woehr |
| 7,226,434 B2 | 6/2007 | Carlyon |
| 7,235,062 B2 | 6/2007 | Brustad |
| 7,238,169 B2 | 7/2007 | Takagi |
| 7,239,169 B2 | 7/2007 | Isa |
| 7,247,148 B2 | 7/2007 | Murashita |
| 7,252,651 B2 | 8/2007 | Haider |
| 7,264,613 B2 | 9/2007 | Woehr |
| 7,291,128 B2 | 11/2007 | Rossi |
| 7,291,130 B2 | 11/2007 | McGurk |
| 7,297,138 B2 | 11/2007 | Fangrow, Jr. |
| 7,300,419 B2 | 11/2007 | Fangrow, Jr. |
| 7,303,548 B2 | 12/2007 | Rhad |
| 7,306,579 B2 | 12/2007 | Fujii |
| 7,309,326 B2 | 12/2007 | Fangrow, Jr. |
| 7,311,693 B2 | 12/2007 | Shekalim |
| 7,311,694 B2 | 12/2007 | Fangrow, Jr. |
| 7,314,462 B2 | 1/2008 | O'Reagan |
| 7,314,463 B2 | 1/2008 | Fangrow, Jr. |
| 7,316,667 B2 | 1/2008 | Lindstrom |
| 7,318,818 B2 | 1/2008 | Yashiro |
| 7,326,189 B2 | 2/2008 | Mori |
| 7,331,934 B2 | 2/2008 | Suresh |
| 7,331,935 B2 | 2/2008 | Barere |
| 7,331,939 B2 | 2/2008 | Fangrow, Jr. |
| 7,341,573 B2 | 3/2008 | Ferguson |
| 7,347,838 B2 | 3/2008 | Kulli |
| 7,347,839 B2 | 3/2008 | Hiejima |
| 7,347,842 B2 | 3/2008 | Thorne |
| 7,354,422 B2 | 4/2008 | Riesenberger |
| 7,357,784 B2 | 4/2008 | Ferguson |
| 7,361,164 B2 | 4/2008 | Simpson |
| 7,371,226 B2 | 5/2008 | Huang |
| 7,371,227 B2 | 5/2008 | Zeiner |
| 7,374,554 B2 | 5/2008 | Menzi |
| 7,387,616 B2 | 6/2008 | Li |
| 7,396,346 B2 | 7/2008 | Nakajima |
| 7,399,293 B2 | 7/2008 | Oyibo |
| 7,407,491 B2 | 8/2008 | Fangrow, Jr. |
| 7,407,495 B2 | 8/2008 | Barere |
| 7,413,562 B2 | 8/2008 | Ferguson |
| 7,422,571 B2 | 9/2008 | Schweikert |
| 7,422,573 B2 | 9/2008 | Wilkinson |
| 7,445,611 B2 | 11/2008 | Osborne |
| 7,458,954 B2 | 12/2008 | Ferguson |
| 7,470,254 B2 | 12/2008 | Basta |
| 7,470,261 B2 | 12/2008 | Lynn |
| 7,470,262 B2 | 12/2008 | Hiejima |
| 7,497,847 B2 | 3/2009 | Crawford |
| 7,497,849 B2 | 3/2009 | Fangrow, Jr. |
| 7,500,965 B2 | 3/2009 | Menzi |
| 7,507,222 B2 | 3/2009 | Cindrich |
| 7,513,887 B2 | 4/2009 | Halseth |
| 7,513,888 B2 | 4/2009 | Sircom et al. |
| 7,524,300 B2 | 4/2009 | Patton |
| 7,530,965 B2 | 5/2009 | Villa |
| 7,534,227 B2 | 5/2009 | Kulli |
| 7,534,231 B2 | 5/2009 | Kuracina |
| 7,537,582 B2 | 5/2009 | Suresh |
| 7,544,181 B2 | 6/2009 | Axelsson |
| 7,566,323 B2 | 7/2009 | Chang |
| 7,566,327 B2 | 7/2009 | Mathias |
| 7,569,033 B2 | 8/2009 | Greene |
| 7,572,247 B2 | 8/2009 | Smith |
| 7,575,570 B2 | 8/2009 | Barere |
| 7,578,803 B2 | 8/2009 | Rome |
| 7,578,805 B2 | 8/2009 | Hwang |
| 7,578,806 B2 | 8/2009 | Zeoli |
| 7,591,449 B2 | 9/2009 | Raines |
| 7,597,681 B2 | 10/2009 | Sutton |
| 7,597,684 B2 | 10/2009 | Alcha |
| 7,601,139 B2 | 10/2009 | Woehr |
| 7,604,616 B2 | 10/2009 | Thoresen |
| 7,608,057 B2 | 10/2009 | Woehr |
| 7,611,485 B2 | 11/2009 | Ferguson |
| 7,611,487 B2 | 11/2009 | Woehr |
| 7,611,488 B2 | 11/2009 | Chang |
| 7,611,499 B2 | 11/2009 | Woehr |
| 7,614,423 B2 | 11/2009 | Yokota |
| 7,618,395 B2 | 11/2009 | Ferguson |
| 7,625,360 B2 | 12/2009 | Woehr |
| 7,628,774 B2 | 12/2009 | Fangrow, Jr. |
| 7,628,776 B2 | 12/2009 | Gibson |
| 7,632,243 B2 | 12/2009 | Bialecki |
| 7,635,352 B2 | 12/2009 | Adams |
| 7,635,357 B2 | 12/2009 | Mayer |
| 7,637,887 B2 | 12/2009 | Woehr |
| 7,637,888 B2 | 12/2009 | Schwarzich |
| 7,637,893 B2 | 12/2009 | Christensen |
| 7,651,476 B2 | 1/2010 | Kohler |
| 7,651,481 B2 | 1/2010 | Raybuck |
| 7,654,988 B2 | 2/2010 | Moulton |
| 7,658,725 B2 | 2/2010 | Bialecki |
| 7,662,134 B2 | 2/2010 | Miller |
| 7,666,170 B2 | 2/2010 | Guala |
| 7,670,317 B2 | 3/2010 | Cindrich |
| 7,670,320 B2 | 3/2010 | Iwase |
| 7,682,331 B2 | 3/2010 | Carrez |
| 7,682,339 B2 | 3/2010 | Fujii |
| 7,682,340 B2 | 3/2010 | Funamura |
| 7,686,784 B2 | 3/2010 | Baik |
| 7,691,088 B2 | 4/2010 | Howell |

(56) References Cited

U.S. PATENT DOCUMENTS

| | | |
|---|---|---|
| 7,694,403 B2 | 4/2010 | Moulton |
| 7,713,242 B2 | 5/2010 | Streifinger |
| 7,713,243 B2 | 5/2010 | Hillman |
| 7,713,250 B2 | 5/2010 | Harding |
| 7,713,256 B2 | 5/2010 | Brimhall |
| 7,713,257 B2 | 5/2010 | Brimhall |
| 7,717,888 B2 | 5/2010 | Vaillancourt |
| 7,722,563 B2 | 5/2010 | Isaacson |
| 7,722,564 B2 | 5/2010 | Vaillancourt |
| 7,722,569 B2 | 5/2010 | Soderholm |
| 7,727,198 B2 | 6/2010 | Nakajima |
| 7,731,687 B2 | 6/2010 | Menzi |
| 7,731,694 B2 | 6/2010 | Becker |
| 7,736,332 B2 | 6/2010 | Carlyon |
| 7,736,337 B2 | 6/2010 | Diep |
| 7,736,339 B2 | 6/2010 | Woehr |
| 7,736,340 B2 | 6/2010 | Harding |
| 7,736,342 B2 | 6/2010 | Abriles |
| 7,740,613 B2 | 6/2010 | Yokoi |
| 7,740,614 B2 | 6/2010 | Murashita |
| 7,744,567 B2 | 6/2010 | Glowacki |
| 7,744,568 B2 | 6/2010 | Douglas |
| 7,744,570 B2 | 6/2010 | Fangrow, Jr. |
| 7,753,338 B2 | 7/2010 | Desecki |
| 7,753,877 B2 | 7/2010 | Bialecki |
| 7,753,887 B2 | 7/2010 | Botich |
| 7,758,543 B2 | 7/2010 | Ferraresi |
| 7,762,986 B2 | 7/2010 | Wang |
| 7,763,199 B2 | 7/2010 | Fangrow, Jr. |
| 7,771,412 B2 | 8/2010 | Anderson |
| 7,785,296 B2 | 8/2010 | Muskatello |
| 7,794,445 B2 | 9/2010 | Dalton |
| 7,794,675 B2 | 9/2010 | Lynn |
| 7,798,994 B2 | 9/2010 | Brimhall |
| 7,806,849 B2 | 10/2010 | Woehr |
| 7,806,858 B2 | 10/2010 | Smith |
| 7,806,869 B2 | 10/2010 | Nilsson |
| 7,806,890 B2 | 10/2010 | McKinnon |
| 7,811,261 B2 | 10/2010 | Rubinstein |
| 7,815,614 B2 | 10/2010 | Fangrow, Jr. |
| 7,824,393 B2 | 11/2010 | Fangrow |
| 7,828,773 B2 | 11/2010 | Swisher |
| 7,828,774 B2 | 11/2010 | Harding |
| 7,833,199 B2 | 11/2010 | Franer |
| 7,850,648 B2 | 12/2010 | Gratwohl |
| 7,850,650 B2 | 12/2010 | Breitweiser |
| 7,850,652 B2 | 12/2010 | Liniger |
| 7,867,204 B2 | 1/2011 | Bartholomew |
| 7,887,516 B2 | 2/2011 | Young |
| 7,892,209 B2 | 2/2011 | Harand |
| 7,892,216 B2 | 2/2011 | Fangrow, Jr. |
| 7,901,379 B2 | 3/2011 | Argentine |
| 7,905,857 B2 | 3/2011 | Swisher |
| 7,914,488 B2 | 3/2011 | Dickerson |
| 7,914,494 B2 | 3/2011 | Hiejima |
| 7,914,519 B2 | 3/2011 | Moran |
| 7,922,698 B2 | 4/2011 | Riesenberger |
| 7,927,314 B2 | 4/2011 | Kuracina |
| 7,931,615 B2 | 4/2011 | Fangrow, Jr. |
| 7,931,622 B2 | 4/2011 | Beling |
| 7,935,080 B2 | 5/2011 | Howell |
| 7,935,090 B2 | 5/2011 | Patton |
| 7,938,805 B2 | 5/2011 | Harding |
| 7,947,018 B2 | 5/2011 | Mckinnon |
| 7,947,032 B2 | 5/2011 | Harding |
| 7,951,119 B2 | 5/2011 | Leeflang |
| 7,951,122 B2 | 5/2011 | Shekalim |
| 7,955,306 B2 | 6/2011 | Wyss |
| 7,959,613 B2 | 6/2011 | Rhad |
| 7,967,797 B2 | 6/2011 | Winsor |
| 7,972,300 B2 | 7/2011 | Smith |
| 7,972,313 B2 | 7/2011 | Woehr |
| 7,976,498 B2 | 7/2011 | Swisher |
| 7,976,502 B2 | 7/2011 | Baid |
| 7,976,503 B2 | 7/2011 | Khan |
| 7,981,090 B2 | 7/2011 | Plishka |
| 7,985,199 B2 | 7/2011 | Kornerup |
| 7,985,232 B2 | 7/2011 | Potter |
| 7,988,664 B2 | 8/2011 | Fiser |
| 7,993,305 B2 | 8/2011 | Ye |
| 7,993,306 B2 | 8/2011 | Marrs |
| 7,998,122 B2 | 8/2011 | Lynn |
| 8,002,765 B2 | 8/2011 | Lopez |
| 8,006,953 B2 | 8/2011 | Bennett |
| 8,016,791 B2 | 9/2011 | Sugiki |
| 8,021,343 B2 | 9/2011 | Nalesso |
| 8,025,646 B2 | 9/2011 | Fukai |
| 8,029,472 B2 | 10/2011 | Leinsing |
| 8,038,647 B2 | 10/2011 | Harding |
| 8,043,263 B2 | 10/2011 | Helgeson |
| 8,043,266 B2 | 10/2011 | Murashita |
| 8,043,316 B2 | 10/2011 | Hardin |
| 8,048,031 B2 | 11/2011 | Shaw |
| 8,048,039 B2 | 11/2011 | Carlyon |
| 8,052,646 B2 | 11/2011 | Schweikert |
| 8,052,647 B2 | 11/2011 | Raulerson |
| 8,052,653 B2 | 11/2011 | Gratwohl |
| 8,062,261 B2 | 11/2011 | Adams |
| 8,066,670 B2 | 11/2011 | Cluff |
| 8,075,529 B2 | 12/2011 | Nakajima |
| RE43,141 E | 1/2012 | Halseth |
| 8,088,104 B2 | 1/2012 | Smith |
| 8,096,973 B2 | 1/2012 | Snow |
| 8,100,857 B2 | 1/2012 | Kuracina |
| 8,100,858 B2 | 1/2012 | Woehr |
| 8,105,276 B2 | 1/2012 | Chen |
| 8,123,738 B2 | 2/2012 | Vaillancourt |
| 8,128,594 B1 | 3/2012 | Chang |
| 8,133,207 B2 | 3/2012 | Wilkinson |
| 8,133,209 B2 | 3/2012 | Guala |
| 8,137,321 B2 | 3/2012 | Argentine |
| 8,147,455 B2 | 4/2012 | Butts |
| 8,157,768 B2 | 4/2012 | Haider |
| 8,162,881 B2 | 4/2012 | Lilley, Jr. |
| 8,162,889 B2 | 4/2012 | Swisher |
| 8,162,904 B2 | 4/2012 | Takano |
| 8,197,452 B2 | 6/2012 | Harding |
| 8,206,355 B2 | 6/2012 | Thorne |
| 8,211,070 B2 | 7/2012 | Woehr |
| 8,226,627 B2 | 7/2012 | Fowles |
| 8,231,525 B2 | 7/2012 | Cohen |
| 8,251,950 B2 | 8/2012 | Albert |
| 8,257,322 B2 | 9/2012 | Koehler |
| 2001/0021821 A1 | 9/2001 | Wang |
| 2001/0021827 A1 | 9/2001 | Ferguson |
| 2001/0039401 A1 | 11/2001 | Ferguson |
| 2002/0010434 A1 | 1/2002 | Larsen |
| 2002/0022803 A1 | 2/2002 | Wemmert |
| 2002/0026154 A1 | 2/2002 | Chang |
| 2002/0065488 A1 | 5/2002 | Suzuki |
| 2002/0065489 A1 | 5/2002 | Novacek |
| 2002/0128604 A1 | 9/2002 | Nakajima |
| 2002/0151850 A1 | 10/2002 | Ferguson |
| 2002/0156428 A1 | 10/2002 | Lee |
| 2003/0060785 A1 | 3/2003 | Lavean |
| 2003/0105431 A1 | 6/2003 | Howell |
| 2003/0114797 A1 | 6/2003 | Vaillancourt |
| 2003/0125676 A1 | 7/2003 | Swenson |
| 2003/0125677 A1 | 7/2003 | Swenson |
| 2003/0130623 A1 | 7/2003 | Chen |
| 2003/0144627 A1 | 7/2003 | Woehr |
| 2003/0181867 A1 | 9/2003 | Bressler |
| 2003/0181869 A1 | 9/2003 | Swenson |
| 2003/0181870 A1 | 9/2003 | Bressler |
| 2003/0181871 A1 | 9/2003 | Wilkinson |
| 2003/0181875 A1 | 9/2003 | Bressler |
| 2003/0195471 A1 | 10/2003 | Woehr |
| 2003/0195479 A1 | 10/2003 | Kuracina |
| 2003/0199827 A1 | 10/2003 | Thorne |
| 2003/0216687 A1 | 11/2003 | Hwang |
| 2003/0229316 A1 | 12/2003 | Hwang |
| 2004/0006313 A1 | 1/2004 | Chian |
| 2004/0019334 A1 | 1/2004 | Ohkubo |
| 2004/0039333 A1 | 2/2004 | Lee |

(56) References Cited

U.S. PATENT DOCUMENTS

| | | |
|---|---|---|
| 2004/0044313 A1 | 3/2004 | Nakajima |
| 2004/0049155 A1 | 3/2004 | Schramm |
| 2004/0078003 A1 | 4/2004 | Smith |
| 2004/0092871 A1 | 5/2004 | Knepshield |
| 2004/0106903 A1 | 6/2004 | Shue |
| 2004/0116857 A1 | 6/2004 | Kiehne |
| 2004/0122378 A1 | 6/2004 | Hsu |
| 2004/0138628 A1 | 7/2004 | Woehr |
| 2004/0147876 A1 | 7/2004 | Maggioni |
| 2004/0171989 A1 | 9/2004 | Horner |
| 2004/0171995 A1 | 9/2004 | Niermann |
| 2004/0186426 A1 | 9/2004 | Allard |
| 2004/0186427 A1 | 9/2004 | Pok |
| 2004/0186434 A1 | 9/2004 | Harding |
| 2004/0204681 A1 | 10/2004 | Thoresen |
| 2004/0225260 A1 | 11/2004 | Villa |
| 2004/0230164 A1 | 11/2004 | Spinks |
| 2004/0236288 A1 | 11/2004 | Howell |
| 2004/0236289 A1 | 11/2004 | Ferguson |
| 2004/0243060 A1 | 12/2004 | Rossi |
| 2004/0243061 A1 | 12/2004 | McGurk |
| 2004/0243066 A1 | 12/2004 | Meyer |
| 2004/0243071 A1 | 12/2004 | Suzuki |
| 2005/0004532 A1 | 1/2005 | Woehr |
| 2005/0027263 A1 | 2/2005 | Woehr |
| 2005/0038385 A1 | 2/2005 | Shen |
| 2005/0038399 A1 | 2/2005 | Suzuki |
| 2005/0043691 A1 | 2/2005 | Ferguson |
| 2005/0049554 A1 | 3/2005 | Chueh |
| 2005/0059933 A1 | 3/2005 | Johnson |
| 2005/0070855 A1 | 3/2005 | Ferguson |
| 2005/0075609 A1 | 4/2005 | Latona |
| 2005/0080378 A1 | 4/2005 | Cindrich |
| 2005/0085745 A1 | 4/2005 | Kitta |
| 2005/0096599 A1 | 5/2005 | Crawford |
| 2005/0119627 A1 | 6/2005 | Crawford |
| 2005/0137528 A1 | 6/2005 | Wilkinson |
| 2005/0137535 A1 | 6/2005 | Gollobin |
| 2005/0159706 A1 | 7/2005 | Wilkinson |
| 2005/0182362 A1 | 8/2005 | Sircom |
| 2005/0215951 A1 | 9/2005 | Saulenas |
| 2005/0234408 A1 | 10/2005 | Chong |
| 2005/0240150 A1 | 10/2005 | Gordon |
| 2005/0267412 A1 | 12/2005 | Wilkinson |
| 2006/0058742 A1 | 3/2006 | Cha |
| 2006/0074384 A1 | 4/2006 | Kohler |
| 2006/0079808 A1 | 4/2006 | Allard |
| 2006/0084916 A1 | 4/2006 | Lo |
| 2006/0106339 A1 | 5/2006 | Mastorakis |
| 2006/0106340 A1 | 5/2006 | Goossens |
| 2006/0116638 A1 | 6/2006 | Woehr |
| 2006/0155245 A1 | 7/2006 | Woehr |
| 2006/0161108 A1 | 7/2006 | Mogensen |
| 2006/0161116 A1 | 7/2006 | Willis |
| 2006/0184115 A1 | 8/2006 | Saied |
| 2006/0189934 A1 | 8/2006 | Kuracina |
| 2006/0200195 A1 | 9/2006 | Yang |
| 2006/0217655 A1 | 9/2006 | Vitullo |
| 2006/0229554 A1 | 10/2006 | Lou |
| 2006/0229556 A1 | 10/2006 | Pressly, Sr. |
| 2006/0229563 A1 | 10/2006 | O'Reagan |
| 2006/0253074 A1 | 11/2006 | Thayer |
| 2006/0253076 A1 | 11/2006 | Butts |
| 2006/0264827 A1 | 11/2006 | Whang |
| 2006/0264828 A1 | 11/2006 | Woehr |
| 2007/0005013 A1 | 1/2007 | Lai |
| 2007/0005014 A1 | 1/2007 | Lin |
| 2007/0016139 A1 | 1/2007 | Breitweiser |
| 2007/0038179 A1 | 2/2007 | Bialecki |
| 2007/0038182 A1 | 2/2007 | Bialecki |
| 2007/0038183 A1 | 2/2007 | Bialecki |
| 2007/0038184 A1 | 2/2007 | Bialecki |
| 2007/0038185 A1 | 2/2007 | Albert |
| 2007/0038186 A1 | 2/2007 | Sutton |
| 2007/0038187 A1 | 2/2007 | Albert |
| 2007/0038188 A1 | 2/2007 | Bialecki |
| 2007/0073221 A1 | 3/2007 | Bialecki |
| 2007/0073222 A1 | 3/2007 | Lilley, Jr. |
| 2007/0073225 A1 | 3/2007 | Lee |
| 2007/0078390 A1 | 4/2007 | Cing-hong |
| 2007/0078397 A1 | 4/2007 | Weststrate |
| 2007/0078404 A1 | 4/2007 | Wu |
| 2007/0078405 A1 | 4/2007 | Lai |
| 2007/0078407 A1 | 4/2007 | Huang |
| 2007/0083162 A1 | 4/2007 | O'Reagan |
| 2007/0083167 A1 | 4/2007 | Smith |
| 2007/0100296 A1 | 5/2007 | Hwang |
| 2007/0100297 A1 | 5/2007 | Woehr |
| 2007/0106231 A1 | 5/2007 | Snow |
| 2007/0118082 A1 | 5/2007 | Mori |
| 2007/0135764 A1 | 6/2007 | Chen |
| 2007/0156093 A1 | 7/2007 | Woehr |
| 2007/0156100 A1 | 7/2007 | Moesli |
| 2007/0161950 A1 | 7/2007 | Carlyon |
| 2007/0179443 A1 | 8/2007 | Johnson aka Mindes |
| 2007/0179446 A1 | 8/2007 | Carrez |
| 2007/0197964 A1 | 8/2007 | Hsu |
| 2007/0197965 A1 | 8/2007 | Hsu |
| 2007/0197966 A1 | 8/2007 | Lee |
| 2007/0197967 A1 | 8/2007 | Lee |
| 2007/0219492 A1 | 9/2007 | Lucas |
| 2007/0232998 A1 | 10/2007 | Yang |
| 2007/0250003 A1 | 10/2007 | Bare |
| 2007/0255212 A1 | 11/2007 | Smith |
| 2007/0270753 A1 | 11/2007 | Kulli |
| 2007/0282268 A1 | 12/2007 | Mayse |
| 2008/0021388 A1 | 1/2008 | Schwarzich |
| 2008/0027381 A1 | 1/2008 | Smith |
| 2008/0065015 A1 | 3/2008 | Fiser |
| 2008/0065025 A1 | 3/2008 | Jenkins |
| 2008/0071213 A1 | 3/2008 | Sircom |
| 2008/0071222 A1 | 3/2008 | Rhad |
| 2008/0086089 A1 | 4/2008 | Isaacson |
| 2008/0097304 A1 | 4/2008 | Thorne |
| 2008/0097342 A1 | 4/2008 | Gordin |
| 2008/0097343 A1 | 4/2008 | Woehr |
| 2008/0097344 A1 | 4/2008 | McKinnon |
| 2008/0097345 A1 | 4/2008 | Ferguson |
| 2008/0103449 A1 | 5/2008 | Murashita |
| 2008/0108944 A1 | 5/2008 | Woehr |
| 2008/0115845 A1 | 5/2008 | Leuliet |
| 2008/0119795 A1 | 5/2008 | Erskine |
| 2008/0140011 A1 | 6/2008 | Hager |
| 2008/0147003 A1 | 6/2008 | Menzi |
| 2008/0154195 A1 | 6/2008 | Huang |
| 2008/0177238 A1 | 7/2008 | Follman |
| 2008/0243086 A1 | 10/2008 | Hager |
| 2008/0249478 A1 | 10/2008 | Ishikura |
| 2008/0249480 A1 | 10/2008 | Riesenberger |
| 2008/0283789 A1 | 11/2008 | Rubio |
| 2008/0312596 A1 | 12/2008 | Murashita |
| 2009/0005743 A1 | 1/2009 | Vaillancourt |
| 2009/0012480 A1* | 1/2009 | Moulton et al. ............... 604/263 |
| 2009/0048566 A1 | 2/2009 | Ferguson |
| 2009/0054852 A1 | 2/2009 | Takano |
| 2009/0082732 A1 | 3/2009 | Hillman |
| 2009/0088696 A1 | 4/2009 | Harding |
| 2009/0093771 A1 | 4/2009 | Hwang |
| 2009/0131876 A1 | 5/2009 | Coyne |
| 2009/0137958 A1 | 5/2009 | Erskine |
| 2009/0143737 A1 | 6/2009 | Kobayashi |
| 2009/0157013 A1 | 6/2009 | Wong |
| 2009/0163861 A1 | 6/2009 | Carlyon |
| 2009/0171285 A1 | 7/2009 | Wang |
| 2009/0177167 A1 | 7/2009 | Kuracina |
| 2009/0182280 A1 | 7/2009 | Glowacki |
| 2009/0216153 A1 | 8/2009 | Srivatsa |
| 2009/0216201 A1 | 8/2009 | Meehan |
| 2009/0227956 A1 | 9/2009 | Emmott |
| 2009/0281499 A1 | 11/2009 | Harding |
| 2009/0281506 A1 | 11/2009 | Mathias |
| 2009/0287154 A1 | 11/2009 | Harding |
| 2009/0292260 A1 | 11/2009 | Vaillancourft |
| 2009/0292261 A1 | 11/2009 | Greene |

(56) References Cited

U.S. PATENT DOCUMENTS

| | | |
|---|---|---|
| 2009/0306591 A1 | 12/2009 | Amisar |
| 2009/0312711 A1 | 12/2009 | Brimhall |
| 2010/0063455 A1 | 3/2010 | Moyer |
| 2010/0069840 A1 | 3/2010 | Suresh |
| 2010/0082002 A1 | 4/2010 | Baid |
| 2010/0087787 A1 | 4/2010 | Woehr |
| 2010/0106092 A1 | 4/2010 | Tanabe |
| 2010/0114035 A1 | 5/2010 | Schubert |
| 2010/0114036 A1 | 5/2010 | Steyn |
| 2010/0137815 A1 | 6/2010 | Kuracina |
| 2010/0191188 A1 | 7/2010 | Harding |
| 2010/0191189 A1 | 7/2010 | Harding |
| 2010/0198152 A1 | 8/2010 | Haindl |
| 2010/0204652 A1 | 8/2010 | Morrissey |
| 2010/0204654 A1 | 8/2010 | Mulholland |
| 2010/0222739 A1 | 9/2010 | Klippenstein |
| 2010/0222745 A1 | 9/2010 | Burkholz |
| 2010/0222746 A1 | 9/2010 | Burkholz |
| 2010/0228197 A1 | 9/2010 | Murashita |
| 2010/0234804 A1 | 9/2010 | Hiejima |
| 2010/0241087 A1 | 9/2010 | Moulton |
| 2010/0249707 A1 | 9/2010 | Woehr |
| 2010/0286611 A1 | 11/2010 | Schraga |
| 2010/0298770 A1 | 11/2010 | Rubinstein |
| 2010/0324484 A1 | 12/2010 | Smith |
| 2010/0331781 A1 | 12/2010 | Millerd |
| 2011/0015573 A1 | 1/2011 | Maan |
| 2011/0015579 A1 | 1/2011 | Swisher |
| 2011/0024664 A1 | 2/2011 | Burnard |
| 2011/0054398 A1 | 3/2011 | Djordjevic |
| 2011/0054402 A1 | 3/2011 | Tanabe |
| 2011/0054403 A1 | 3/2011 | Tanabe |
| 2011/0060286 A1 | 3/2011 | Tanabe |
| 2011/0060294 A1 | 3/2011 | Baid |
| 2011/0066107 A1 | 3/2011 | Stephens |
| 2011/0066197 A1 | 3/2011 | Jaax |
| 2011/0092914 A1 | 4/2011 | Clayson |
| 2011/0098641 A1 | 4/2011 | Haider |
| 2011/0118673 A1 | 5/2011 | Dringenberg |
| 2011/0125056 A1 | 5/2011 | Merchant |
| 2011/0152782 A1 | 6/2011 | Jones |
| 2011/0152832 A1 | 6/2011 | Foshee |
| 2011/0160662 A1 | 6/2011 | Stout |
| 2011/0160663 A1 | 6/2011 | Stout |
| 2011/0160675 A1 | 6/2011 | Ruan |
| 2011/0208124 A1 | 8/2011 | Rhad |
| 2011/0208126 A1 | 8/2011 | Riemelmoser |
| 2011/0208133 A1 | 8/2011 | Woehr |
| 2011/0213307 A1 | 9/2011 | Kawai |
| 2011/0264037 A1 | 10/2011 | Foshee |
| 2011/0264040 A1 | 10/2011 | Li |
| 2011/0275991 A1 | 11/2011 | Thayer |
| 2011/0282285 A1 | 11/2011 | Blanchard |
| 2011/0282286 A1 | 11/2011 | Argentine |
| 2011/0301542 A1 | 12/2011 | Schwartz |
| 2011/0301551 A1 | 12/2011 | Koehler |
| 2011/0319820 A1 | 12/2011 | Teoh |
| 2012/0016301 A1 | 1/2012 | Stout |
| 2012/0016302 A1 | 1/2012 | Stout |
| 2012/0022498 A1 | 1/2012 | Smith |
| 2012/0035552 A1 | 2/2012 | Woehr |
| 2012/0041374 A1 | 2/2012 | Lee |
| 2012/0046620 A1 | 2/2012 | Woehr |
| 2012/0046621 A1 | 2/2012 | Vaillancourt |
| 2012/0059323 A1 | 3/2012 | Moberg |
| 2012/0059325 A1 | 3/2012 | Cluff |
| 2012/0078200 A1 | 3/2012 | Woehr |
| 2012/0130321 A1 | 5/2012 | Woehr |
| 2012/0136311 A1 | 5/2012 | Knutsson |
| 2012/0143138 A1 | 6/2012 | King |
| 2012/0143151 A1 | 6/2012 | Low |
| 2012/0184910 A1 | 7/2012 | Woehr |
| 2012/0197201 A1 | 8/2012 | Tanabe |
| 2012/0215179 A1 | 8/2012 | Halili |
| 2012/0220956 A1 | 8/2012 | Kuracina |
| 2012/0220957 A1 | 8/2012 | Kuracina |

OTHER PUBLICATIONS

International Search Report dated Dec. 17, 2012 in copending International Application No. PCT/2012/055295.
International Search Report dated Dec. 19, 2012 in copending International Application No. PCT/US2012/056979.
U.S. Appl. No. 13/616,464, filed Sep. 14, 2012, Tremblay.
U.S. Appl. No. 13/625,957, filed Sep. 25, 2012, Finnestad et al.
U.S. Appl. No. 13/651,979, filed Oct. 15, 2012, Walker et al.
11.Km-02422(a) (1502.562) ri International Search Report dated Jan. 16, 2013 in copending International Application No. PCT/US2012/060240.

\* cited by examiner

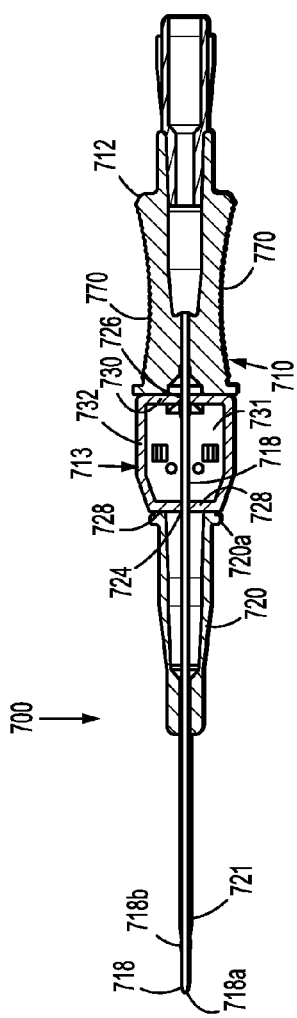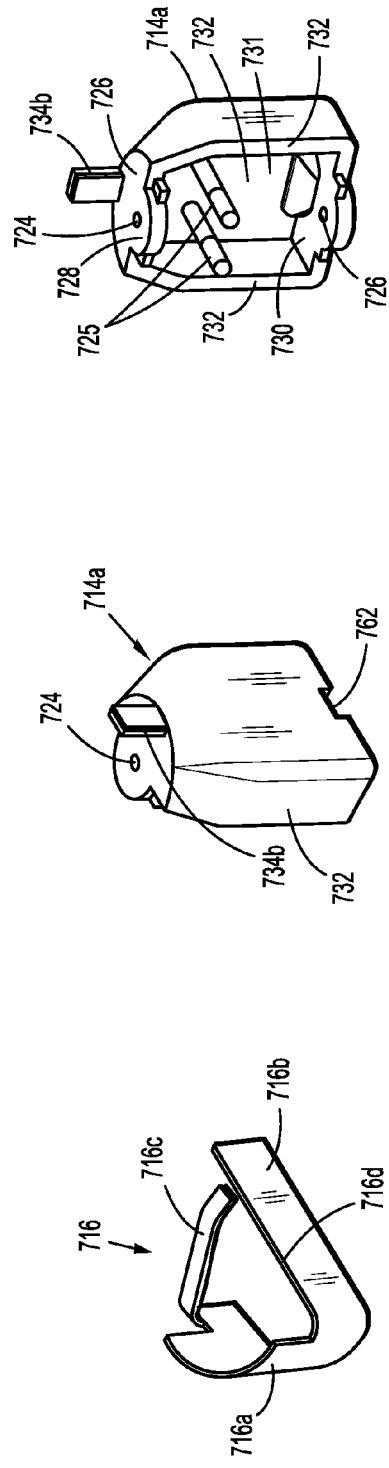

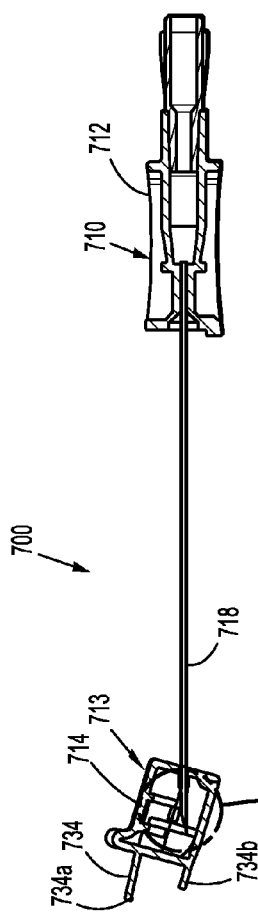
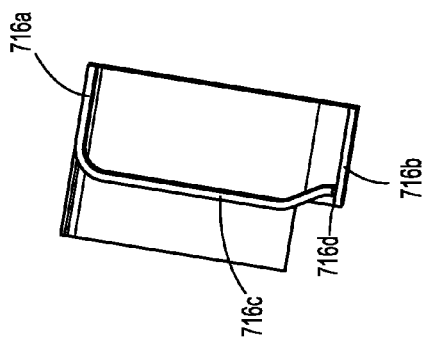
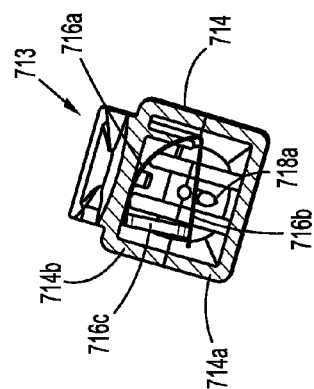
FIG. 10
FIG. 11
FIG. 12
FIG. 13

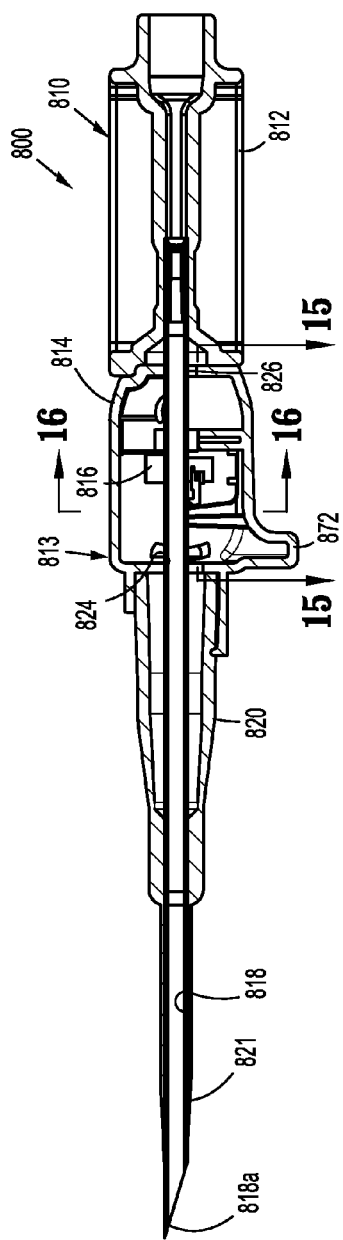
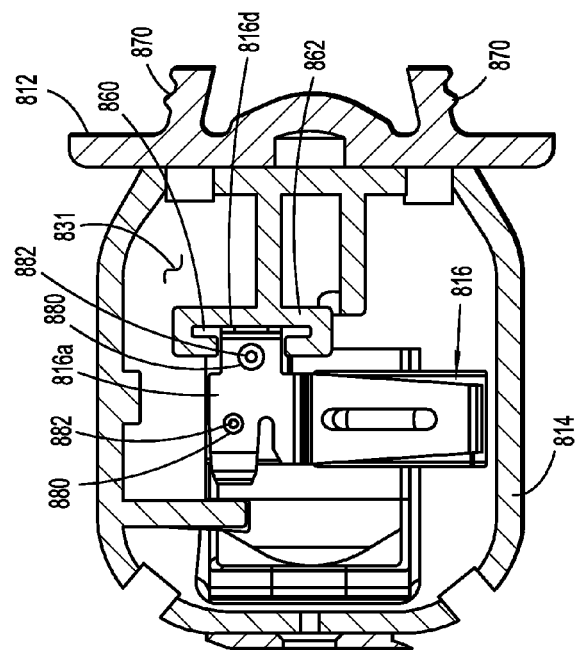
FIG. 14
FIG. 15

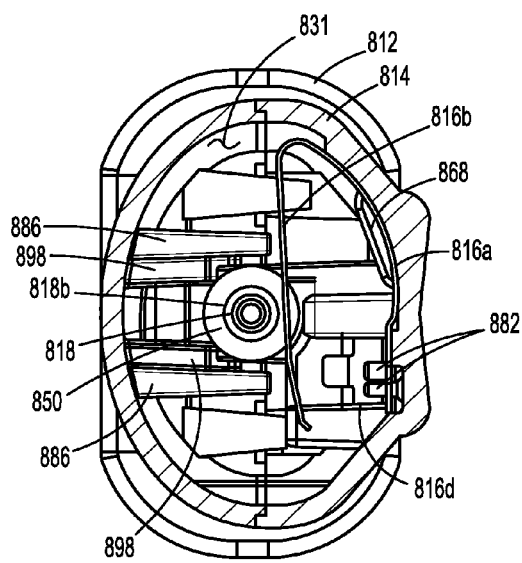
FIG. 16
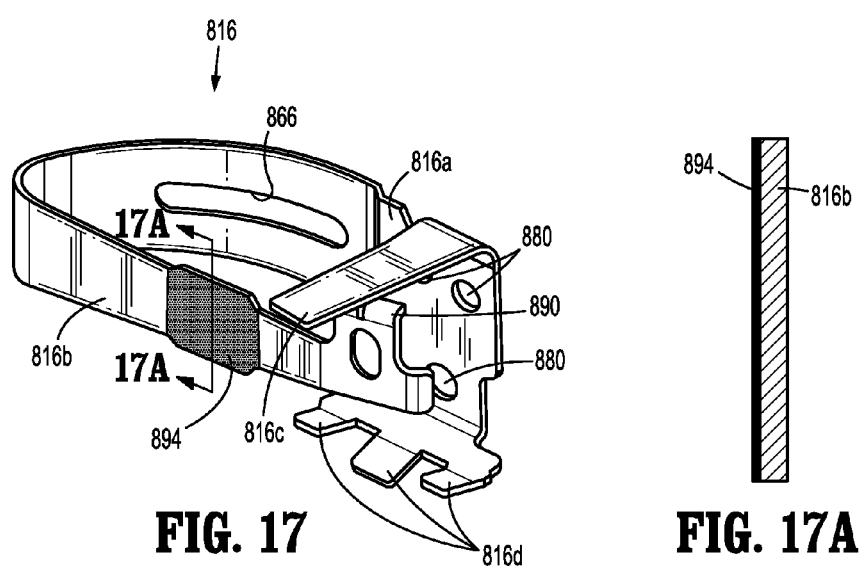
FIG. 17
FIG. 17A

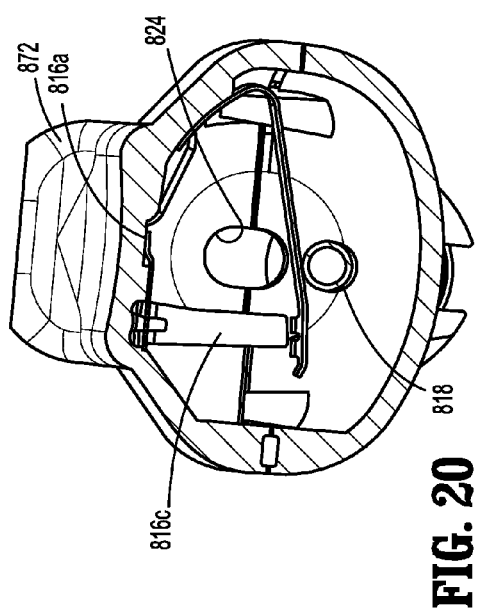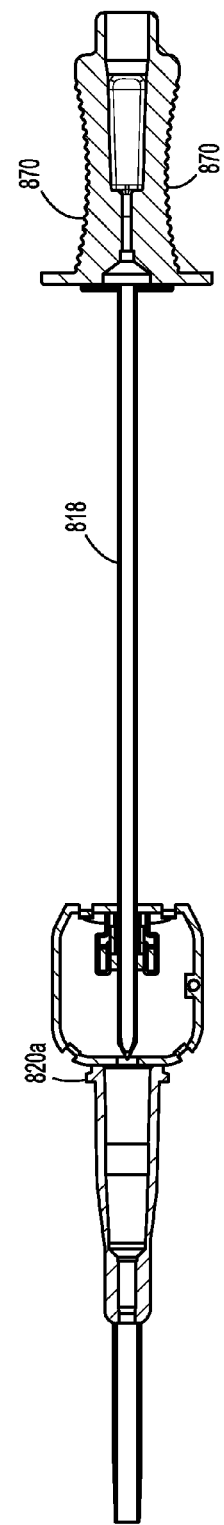
FIG. 20
FIG. 21

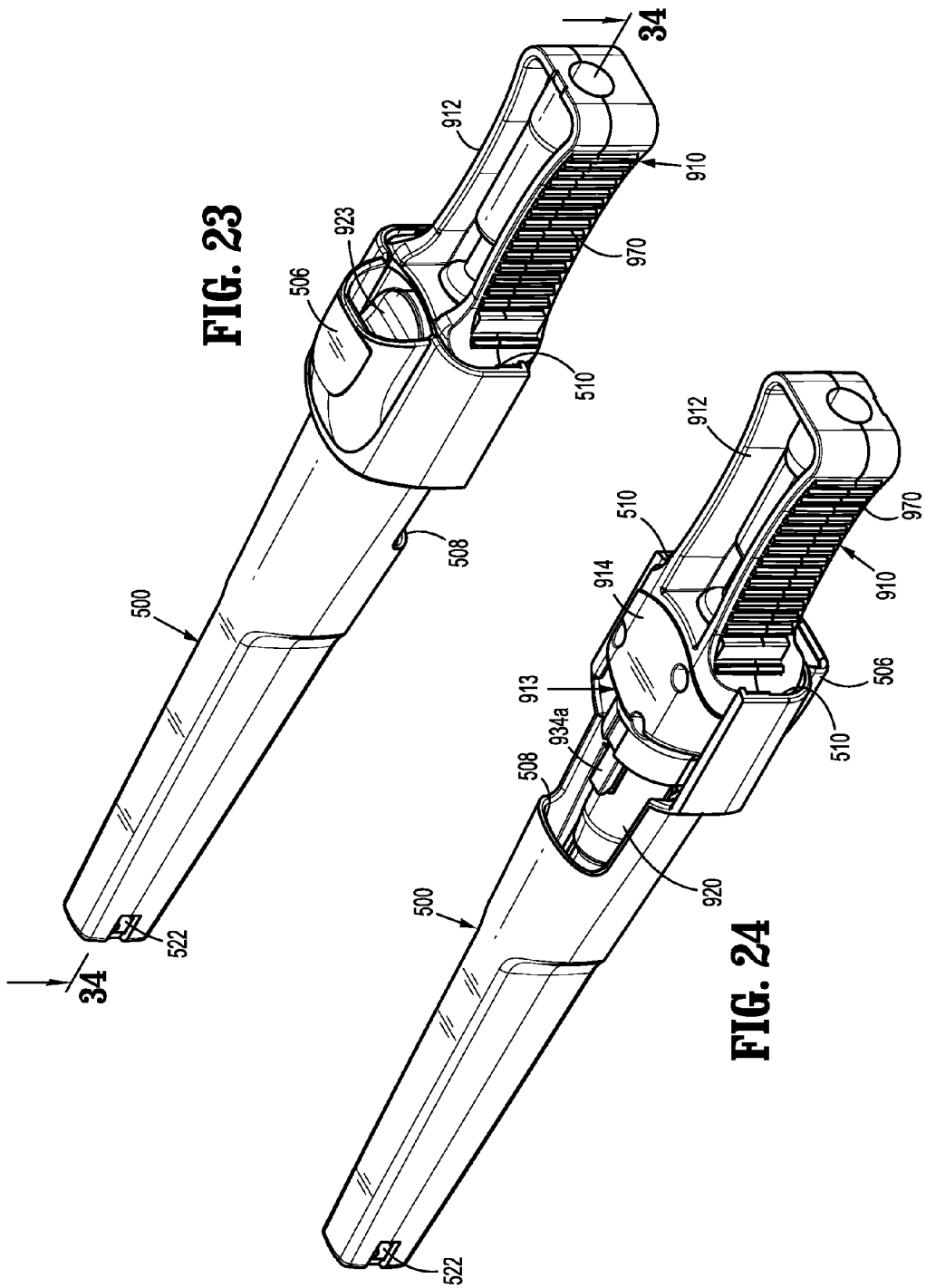

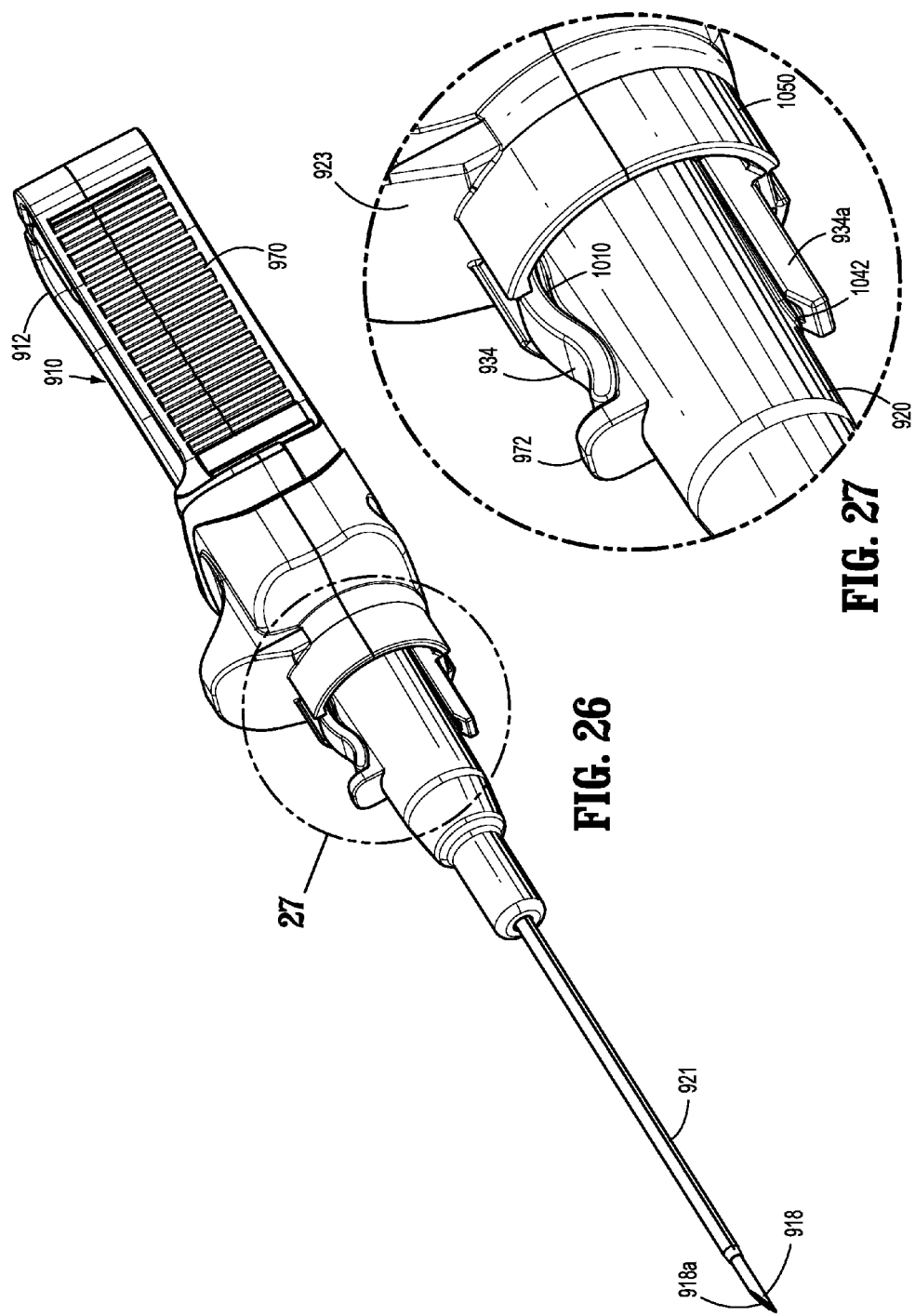

VASCULAR ACCESS ASSEMBLY AND SAFETY DEVICE

CROSS-REFERENCE TO RELATED APPLICATION

This application claims priority to, and the benefit of, U.S. Provisional Patent Application No. 61/547,410, filed on Oct. 14, 2011, the entire contents of which are hereby incorporated by reference.

BACKGROUND

1. Technical Field

The present disclosure relates to intravenous ("IV") catheter assemblies for vascular access, and more particularly to safety IV catheter assemblies for vascular access which include a needle tip guard for protecting a clinician from accidental needle stick injuries.

2. Background of Related Art

IV catheter assemblies are utilized in a variety of medical applications for supplying or withdrawing fluid to or from a body vessel. Generally, IV catheter assemblies include an external cannula for indwelling in a blood vessel of a patient and an internal needle that is inserted into the external cannula to facilitate piercing of the blood vessel of the patient. In operation of the IV catheter assembly, the internal needle is inserted into the external cannula such that the tip portion of the internal needle protrudes from a tip portion of the external cannula. Next, the internal needle is manipulated to pierce a blood vessel and to position the external cannula within the blood vessel. While the external cannula is positioned within the blood vessel, the internal needle is withdrawn from the external cannula leaving the external cannula positioned within the blood vessel. In this position, a medical device can be connected to the rear end portion of the external cannula using, for example, a luer connector, to facilitate the supply and withdrawal of fluid, such as blood, medication and/or nutrients, to or from the blood vessel.

After the internal needle is withdrawn from the external cannula, the exposed needle tip of the internal needle creates a danger of accidental needle stick injury which can leave a clinician vulnerable to the transmission of various blood-borne pathogens, such as HIV and hepatitis. While needle tip protectors have been developed to protect the clinician from needle stick injuries, the cost, ease of use, and effectiveness of these needle tip protectors leaves room for improvement.

Accordingly, it would be beneficial to provide a safety IV catheter assembly which is easily activated by a clinician, effectively protects a clinician from accidental needle stick injury and is economical to produce.

SUMMARY

A safety intravenous catheter assembly is disclosed which comprises a needle assembly, a catheter assembly and a safety device. The needle assembly includes a needle hub and a needle having a proximal end secured to the needle hub and a distal end defining a tip. The catheter assembly includes a catheter hub and a catheter tube extending distally from the catheter hub, and the safety device includes a housing defining a cavity, a distal opening and a proximal opening and a biasing member supported within the cavity. The distal and proximal openings are dimensioned to receive the needle. The biasing member includes a stationary portion, a movable portion and a blocking arm. The movable portion is movable in relation to the stationary portion from a first position to a second position. In an assembled state, the safety device is positioned between the needle hub and the catheter hub, the needle extends through the proximal and distal openings of the housing of the safety device and the catheter assembly, and the biasing member is compressed between the needle and the housing such that the movable portion is in the first position in engagement with the needle. In a disassembled state, the tip of the needle is withdrawn through the distal opening into the cavity of the housing of the safety device and the movable portion of the biasing member is in the second position spaced further outwardly of the stationary portion such that the housing is tilted in relation to the needle. In the tilted position, the needle is moved out of alignment with the distal opening of the housing. In the disassembled state, the blocking arm is positioned between the movable portion and the stationary portion to prevent movement of the movable portion from the second position back to the first position.

In one embodiment, the housing includes at least one post extending from one side of the housing across the cavity which is positioned to engage the stationary portion of the biasing member to secure the position of the biasing member within the housing.

The housing of the safety device may include a finger configured to releasably engage the catheter hub. The finger includes radial projection which is configured to be received in a recess formed in the catheter hub to releasably secure the safety device to the catheter hub.

In one embodiment, the biasing member is unitarily formed from a resilient material such as spring steel.

The needle hub may include a tab and the housing of the safety device may define a cutout positioned to receive the tab in the assembled state to properly orient the safety device in relation to the needle hub.

In one embodiment, the housing is formed from molded half-sections, and the at least one post is formed on one of the half-sections and extends across the cavity towards a sidewall of the other of the half-sections.

The proximal end of the catheter hub may include a luer connector.

In one embodiment, the portion of the movable portion of the biasing member in engagement with the needle may be formed of or covered with a material having a low coefficient of friction. In one embodiment, the movable portion of the biasing member is at least partially covered by a UV cured adhesive.

The biasing member may include spring fingers which are received within a channel formed in the housing to secure the biasing member within the housing.

In one embodiment, the stationary portion of the biasing member defines at least one opening to receive a post formed in the housing to properly align the biasing member within the housing.

A safety device is also disclosed which comprises a housing defining a cavity having a distal opening and a proximal opening. The distal and proximal openings are dimensioned to receive a needle of an intravenous catheter assembly. A biasing member is supported within the cavity and includes, a stationary portion, a movable portion, and a blocking arm. The movable portion is movable from a first position in which the biasing member is compressed between the needle and the housing to a second position in which the movable portion is spaced further outwardly of the stationary portion to tilt the housing in relation to the needle and move the needle out of alignment with the distal opening of the housing. In the second position, the blocking arm of the movable portion is positioned to prevent movement of the movable portion back to the first position.

In one embodiment, the housing includes at least one post extending from one side of the housing across the cavity which is positioned to engage the stationary portion of the biasing member.

The housing of the safety device may include a finger configured to releasably engage a catheter hub which includes radial projection which is configured to be received in a recess formed in the catheter hub to releasably secure the safety device to the catheter hub.

In one embodiment, the biasing member is unitarily formed from a resilient material such as spring steel.

In one embodiment, the housing of the safety device defines a cutout positioned to receive a tab formed on a needle hub to properly orient the safety device in relation to the needle hub.

In one embodiment, the housing is formed from molded half-sections.

In one embodiment, the portion of the movable portion of the biasing member in engagement with the needle may include or be covered with a material having a low coefficient of friction. In one embodiment, the material may include an UV cured adhesive.

In one embodiment, the biasing member includes spring fingers which are received within a channel formed in the housing to secure the biasing member within the housing.

The stationary portion of the biasing member may define at least one opening dimensioned to receive a post formed in the housing to properly align the biasing member within the housing.

BRIEF DESCRIPTION OF THE DRAWINGS

Various embodiments of the presently disclosed safety IV catheter assembly will be described herein with references to the accompanying drawings, wherein:

FIG. 1A is a side cross-sectional view of the safety IV catheter assembly shown in FIG. 1;

FIG. 2A is a perspective view from one side of a half-section of the safety device housing of the safety IV catheter assembly shown in FIG. 1;

FIG. 2B is a perspective view from the other side of the half-section of the safety device housing shown in FIG. 2A;

FIG. 3A is a perspective view of the biasing member of the safety IV catheter assembly shown in FIG. 1;

FIG. 10 is a side cross-sectional view of the needle assembly and safety device of the safety IV catheter assembly shown in FIG. 6 with the safety device supported on the tip of the needle;

FIG. 11 is a transverse, cross-sectional view through the safety device shown in FIG. 10 with the safety device supported on the tip of the needle;

FIG. 12 is an enlarged view of the indicated area of detail shown in FIG. 10;

FIG. 13 is a side view of the biasing member of the safety IV catheter assembly shown in FIG. 10 in its undeformed state;

FIG. 14 is a side cross-sectional view of another embodiment of the presently disclosed safety IV catheter assembly in an assembled state;

FIG. 15 is a cross-sectional view taken along section lines 15-15 of FIG. 14;

FIG. 16 is a transverse cross-sectional view taken along section lines 16-16 of FIG. 14;

FIG. 17 is a side perspective view of the biasing member of the safety IV catheter assembly shown in FIG. 14 with the movable portion in its biased position;

FIG. 17A is a cross-sectional view taken along section lines 17A-17A of FIG. 17;

FIG. 20 is a cross-sectional view taken along section lines 20-20 of FIG. 19;

FIG. 21 is a side cross-sectional view of the safety IV catheter assembly shown in FIG. 14 immediately prior to withdrawal of the needle tip through the distal opening of the housing of the safety device and prior to separation of the safety device from the catheter hub;

FIG. 23 is a top side perspective view from the proximal end of the safety IV catheter assembly shown in FIG. 22;

FIG. 24 is a bottom, perspective view from the proximal end of the safety IV catheter assembly shown in FIG. 22;

FIG. 26 is a side perspective view of the safety IV catheter assembly shown in FIG. 25 with the safety cover removed;

FIG. 27 is an enlarged perspective view of the indicated area of detail shown in FIG. 26;

FIG. 37A is a side view of the needle assembly shown in FIG. 37 with the safety device supported on the needle tip;

FIG. 37B is an enlarged view of the indicated area of detail shown in FIG. 37a;

DETAILED DESCRIPTION OF EMBODIMENTS

Figure 1:
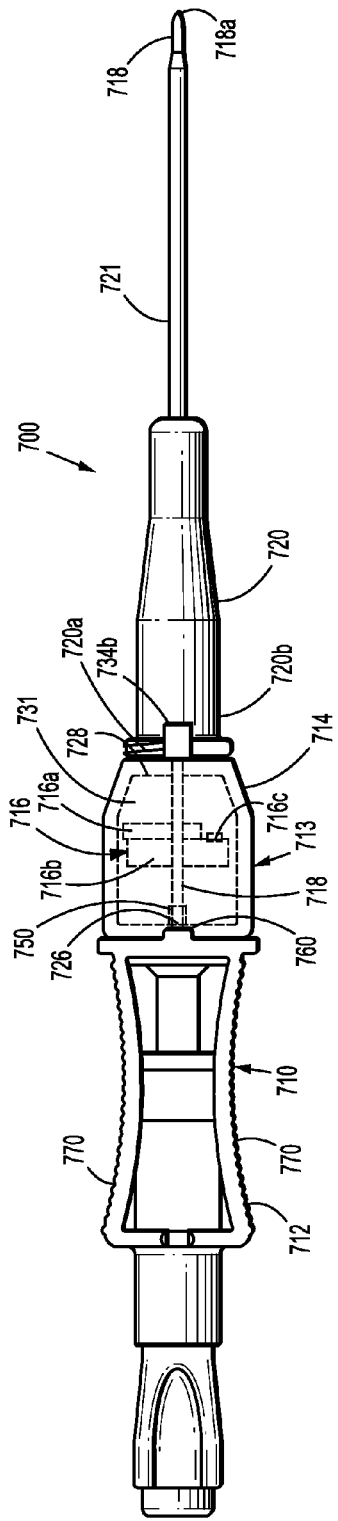
FIG. 1 is a side view of one embodiment of the presently disclosed safety IV catheter assembly in an assembled state with the portion of the biasing member and needle positioned within the safety device housing shown in phantom.

Embodiments of the presently disclosed safety IV catheter assembly will now be described in detail with reference to the drawings wherein like reference numerals designate identical or corresponding elements in each of the several views. In this description, the term "proximal" is generally used to refer to the portion of the device that is closer to a clinician, while the term "distal" is generally used to refer to the portion of the device that is farther from the clinician. As used herein, the term "patient" should be understood as referring to a human patient or other animal, and the term "clinician" should be understood as referring to a doctor, nurse or other care provider and may include support personnel.

FIGS. 1-13 illustrate one embodiment of the presently disclosed safety IV catheter assembly shown generally as 700. As shown in FIGS. 1 and 1A, catheter assembly 700 comprises a needle assembly 710 including a needle hub 712 supporting a distally extending needle 718, a safety device 713 including a housing 714 and a biasing member 716, and a catheter assembly including a catheter hub 720 and a catheter tube 721 extending distally from the catheter hub 720. A proximal end of catheter hub 720 may include a luer connector 720a or the like for releasably securing the catheter hub 720 to a medical device such as a syringe. The needle hub 712 includes gripping surfaces 770 (FIG. 1) and the catheter hub 720 includes a finger engagement member 772 (FIG. 4). Gripping surfaces 770 and finger engagement member 772 facilitate manipulation of the catheter assembly 700 and assist in the separation of the catheter hub 720 from safety device 713 and needle assembly 710. The gripping surfaces 770 may be ribbed or include other known slip-resistant features. In a ready-to-use position, the housing 714 of the safety device 713 is supported between the needle hub 712 and the catheter hub 720 and the needle 718 extends from the needle hub 712 through the safety device housing 714 and the catheter hub 720 such that a tip 718a of needle 718 projects from a distal end of the catheter tube 721.

Figure 3:
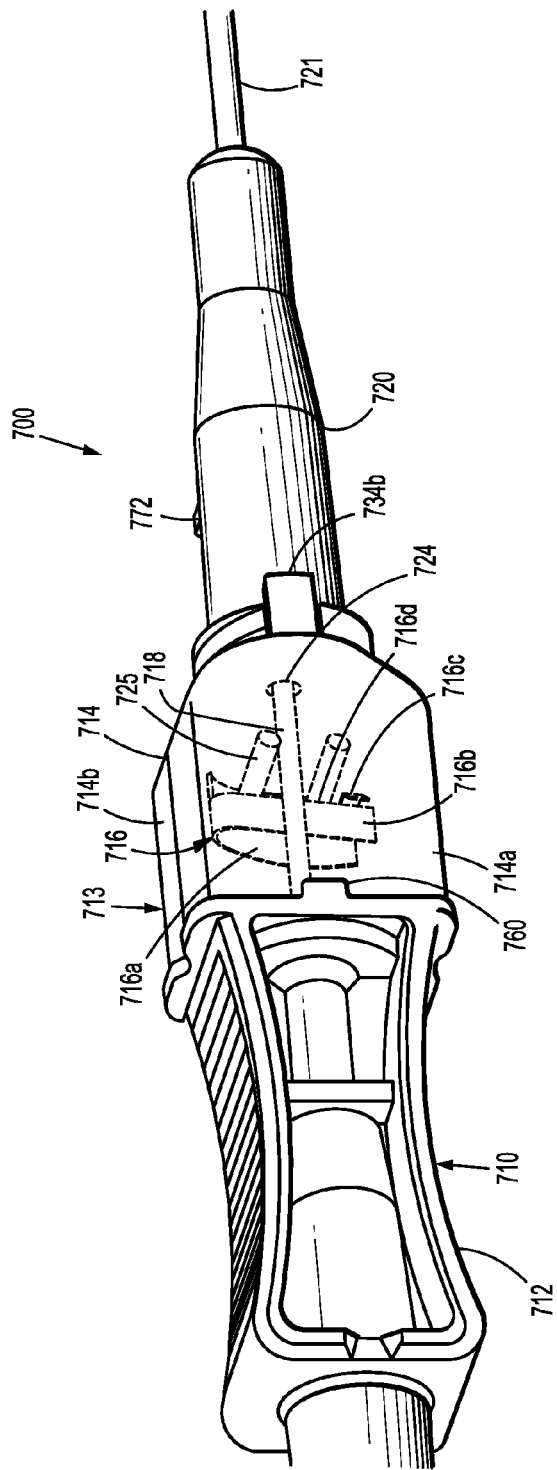
FIGS. 3 and 4 are side perspective views of the safety IV catheter assembly shown in FIG. 1 in an assembled state with the portion of the biasing member and needle positioned within the safety device housing shown in phantom.
Figure 4:
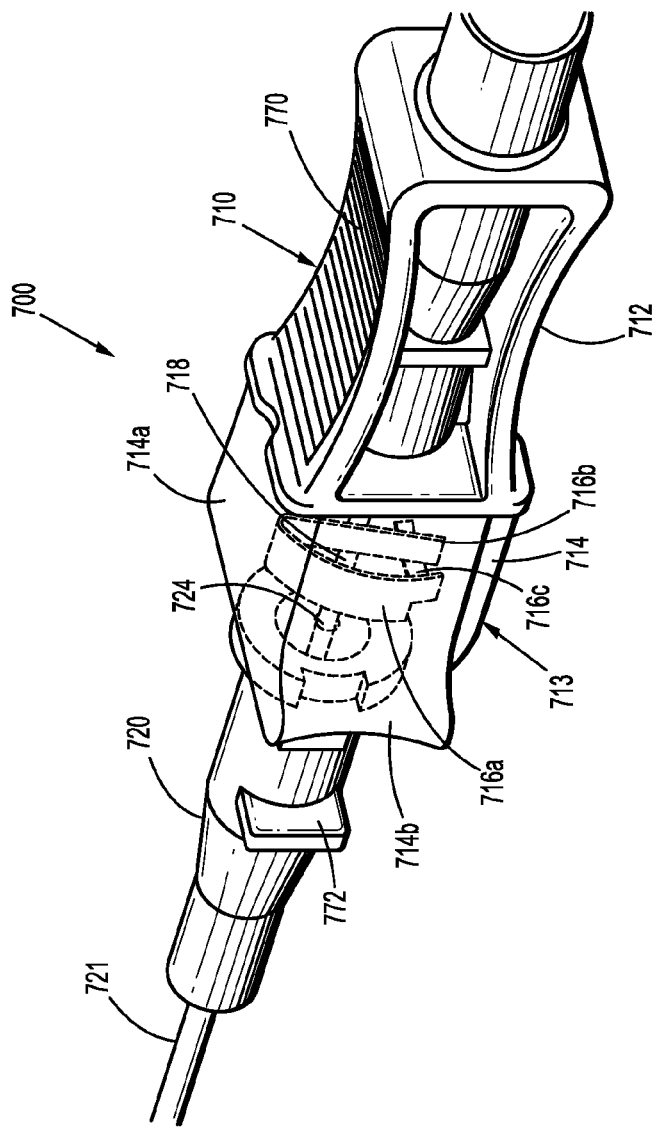
Figure 5:
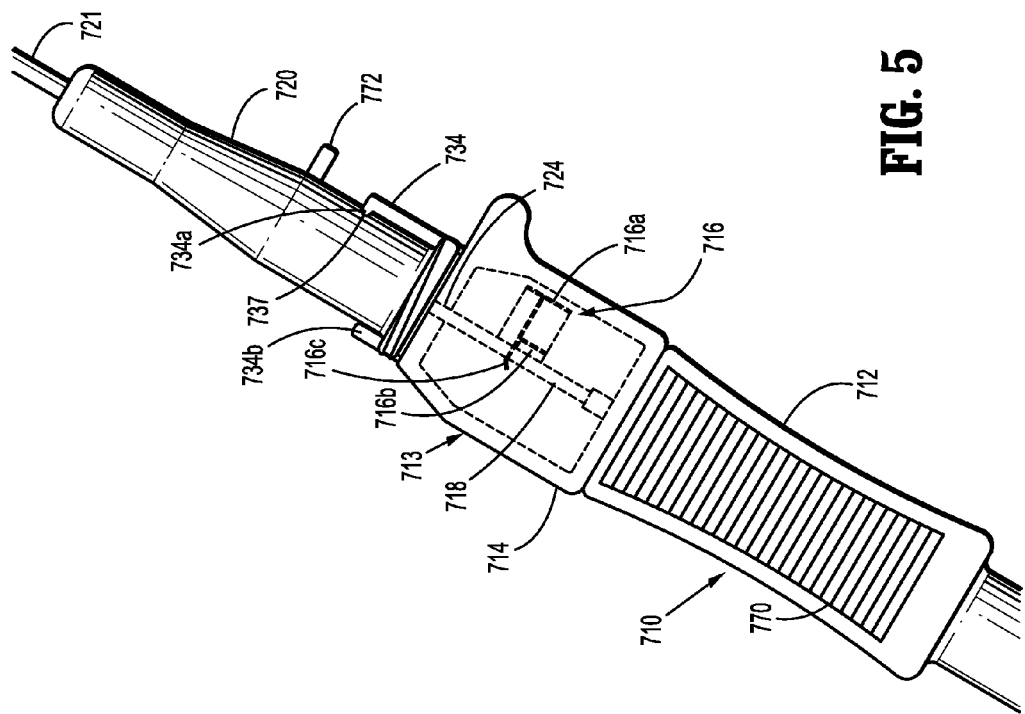
FIG. 5 is a side view of the safety IV catheter assembly shown in FIG. 4 with the portion of the needle and biasing member within the safety device housing shown in phantom.
Figure 6:
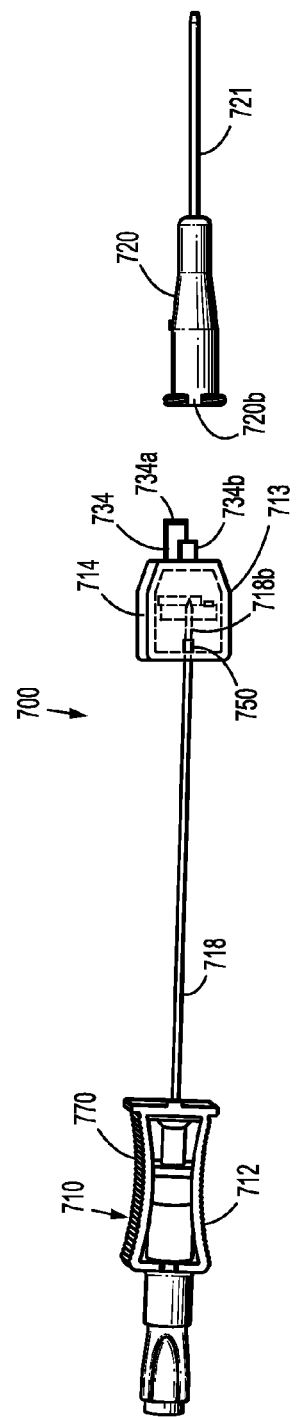
FIG. 6 is a side view of the safety IV catheter assembly shown in FIG. 1 in a disassembled state with the safety device supported on the distal end of the needle and the portion of the biasing member and needle within the safety device housing shown in phantom.
Figure 7:
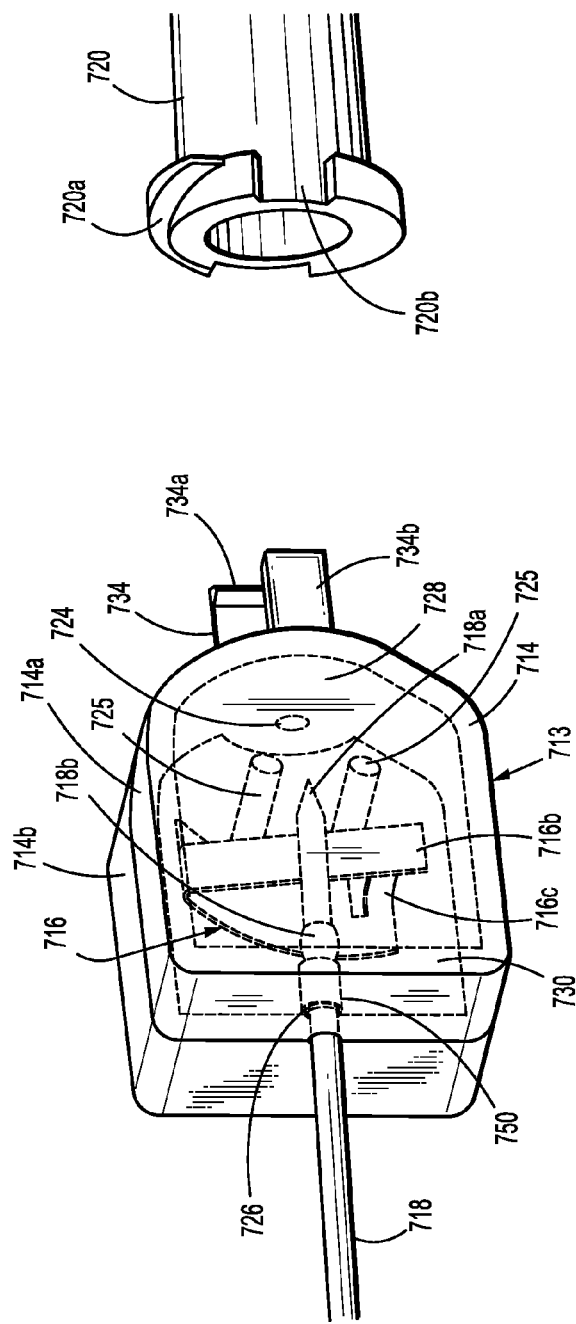
FIG. 7 is an enlarged, side, perspective view of the safety device of the safety IV catheter assembly shown in FIG. 6 supported on a distal end of the needle with the portion of the biasing member and needle positioned within the safety device housing shown in phantom.
Figure 8:
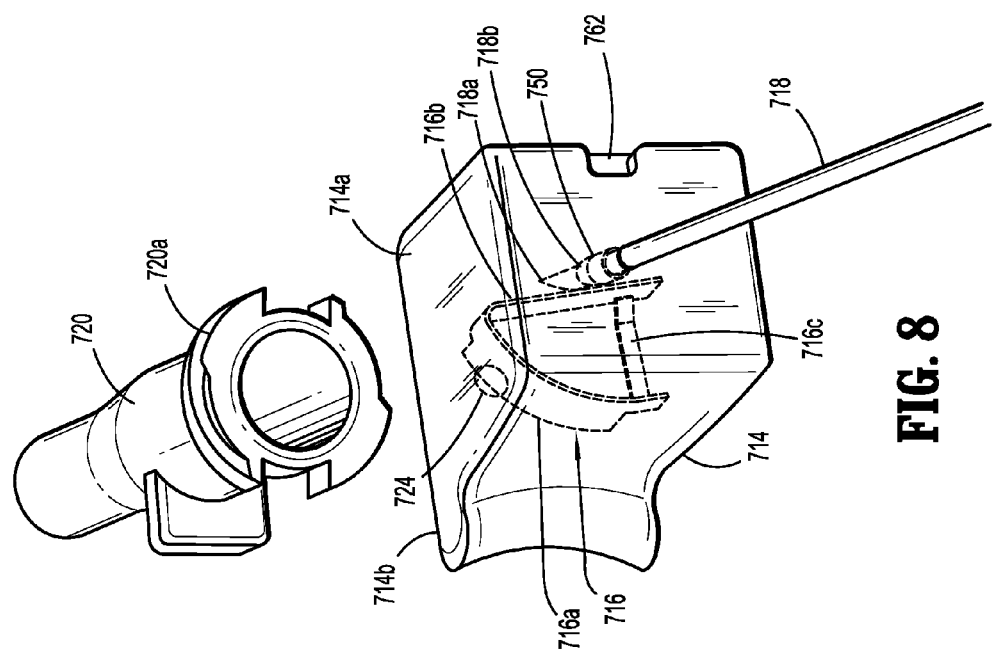
FIG. 8 is a perspective view from the proximal end of the safety IV catheter assembly shown in FIG. 6 in a disassembled state with the portion of the biasing member and needle tip shown in phantom within the safety device housing.
Figure 9:
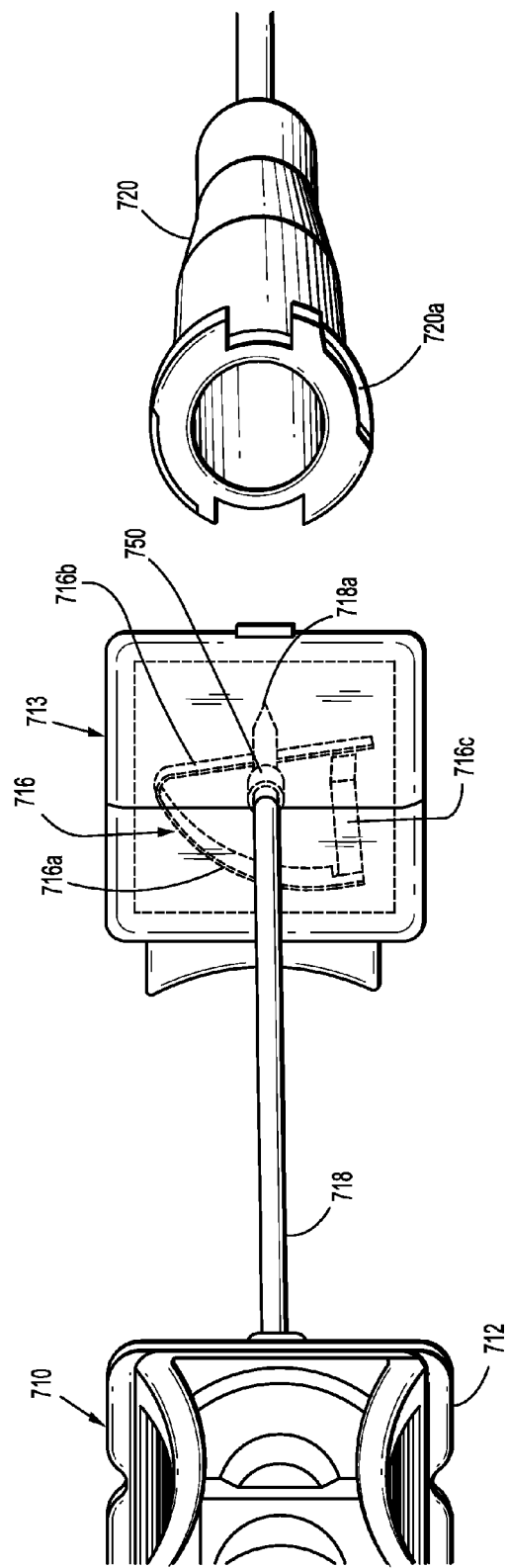
FIG. 9 is a side, partial perspective view of the safety IV catheter assembly shown in FIG. 6 in a disassembled state with the portion of the biasing member and the needle tip shown in phantom within the safety device housing.

Referring also to FIGS. 2A-3, the distal end of needle hub 712 includes a tab 760 (FIG. 3) which is received within a cutout 762 (FIG. 2A) formed in the safety device housing 714 to properly orient the safety device 713 in relation to the needle assembly 710 in the ready-to-use position. Likewise, the safety device housing 714 includes a tab 734b which is received in a slot 720b (FIG. 7) formed in luer connector 720a of catheter hub 720 to properly orient the safety device 713 in relation to the catheter assembly 710.

Referring to FIGS. 2A-5, the safety clip housing 714 may be formed from molded half-sections 714a and 714b (FIG. 3). The housing 714 defines a distal opening 724 and a proximal opening 726 which are defined in a distal wall 728 and a proximal wall 730, respectively, of housing 714. Sidewalls 732 enclose a cavity 731. The biasing member 716 is supported within cavity 731 defined by housing 714 between a sidewall 732 and needle 718 when catheter assembly 700 is in an assembled state. A pair of posts 725 are provided on an inner surface of molded half-section 714a (FIG. 2B). Posts 725 extend across cavity 731 and press a stationary portion 716a of biasing member 716 against a sidewall of housing 714 to fixedly secure biasing member 716 within housing 714. In the assembled state or ready-to-use position of access assembly 700 shown in FIGS. 1-5, needle 718 extends through distal and proximal openings 724 and 726 of housing 714 and biasing member 716 is compressed between a sidewall 732 and needle 718.

Molded half-section 714b of housing 714 also includes a finger 734 (FIG. 5) including a radial projection 734a which is received in a recess 737 formed in catheter hub 720 to releasably secure safety device 713 to catheter hub 720. Finger 734 also extends through a slot 720b (FIG. 7) formed through luer connector 720a to properly orient safety device 713 in relation to catheter hub 720 when the catheter assembly 700 is in an assembled state.

Referring to FIGS. 3-3A, the biasing member 716 includes stationary portion 716a, a resilient arm or movable portion 716b and a blocking arm 716c. In one embodiment, the biasing member 716 is unitarily formed from a resilient material such as spring steel. Alternately, the use of other methods and materials of construction are envisioned.

In the assembled state of safety IV catheter assembly 700 shown in FIGS. 1-5, the stationary portion 716a of biasing member 716 is fixedly held within cavity 731 of housing 714 by posts 725 which extend from housing half-section 714a towards half-section 714b and press stationary portion 716a against a sidewall 732 of housing half section 714b. Alternately, biasing member 716 can be secured within cavity 731 of housing 714 using other known fastening techniques. Movable portion 716b of biasing member 716 is urged towards stationary portion 716a via engagement with needle 718, such that movable portion 716b is maintained in a deformed position slidably engaged with needle 718. Blocking arm 716c is positioned on a top edge 716d of movable portion 716b and extends beyond movable portion 716b. See FIG. 3. The blocking arm 716c is resilient and is maintained in an outwardly deformed state via engagement with top edge 716d of movable portion 716b.

Referring to FIGS. 6-13, when needle assembly 710 is moved proximally in relation to safety device 713 and needle assembly 710, needle 718 is retracted to withdraw tip 718a of needle 718 into housing 714. When needle tip 718a passes through distal opening 724 (FIG. 7) of housing 714 of safety device 713, movable portion 716b of biasing member 716 returns to its undeformed state and moves outwardly from stationary portion 716a to tilt the housing 714 with respect to needle 718. More specifically, due to the inherent characteristics of the resilient material used to form the biasing member 716, movable portion 716b moves outwardly from stationary portion 716a against the needle 718 to tilt the housing 714 in relation to the needle 718 such that the distal opening 724 of housing 714 becomes misaligned with the longitudinal axis of needle 718. In the outward or undeformed position of the biasing member 716, the needle tip 718a is positioned adjacent distal wall 728 of housing 714 offset from distal opening 724. After housing 714 is tilted by the biasing member 716, projection 734a of finger 734 can be manually disengaged from the recess 737 in catheter hub 720 to release housing 714 of safety device 713 from catheter hub 720.

When movable portion 716b of biasing member 716 moves outwardly of stationary portion 716a to a position wherein movable portion 716b passes over the end of blocking arm 716c, blocking arm 716c returns to its undeformed position between movable portion 716b and stationary portion 716a of biasing member 716 (FIG. 13). More specifically, when movable portion 716b of biasing member 716 moves across cavity beyond the free end of blocking arm 716c, blocking arm 716c moves off of edge 716d of movable portion 716b downwardly to a position between stationary portion 716a and movable portion 716b. In this position, blocking arm 716c prevents movable portion 716b from moving back towards stationary portion 716a and, thus, prevents untilting of housing 714 in relation to needle 718. See FIGS. 11 and 13. By preventing the housing 714 from untilting, the needle 718 is prevented from moving back into alignment with the distal opening 724 to prevent the needle tip 718a from exiting housing 714 of safety device 713.

As shown in FIGS. 7-12, in one embodiment needle 718 includes a crimp 718b and a bushing 750 slidably positioned about needle 718 proximally of crimp 718b. The inside diameter of bushing 750 is larger than the outside diameter of needle 718 but smaller than the outside diameter of crimp 718b such that bushing 750 is slidably disposed about needle 718 proximally of crimp 718b. In addition, the outer diameter of bushing 750 is larger than the inner diameter of proximal opening 726. Thus, as needle 718 is being withdrawn through proximal opening 726 of housing 714, crimp 718b engages bushing 750 and retracts bushing 750 with needle 718 proximally until bushing 750 engages proximal wall 730 of housing 714 of safety device 713. At this point, engagement between bushing 750 and wall 730 will prevent further withdrawal of needle 718 through proximal opening 726 of housing 714 to safely retain needle tip 718a within housing 714 of safety device 713. In an alternative embodiment, the bushing 750 need not be provided and crimp 718 can be sized to prevent passage of needle 718 through proximal opening 726.

FIGS. 14-21 illustrate an alternate embodiment of the presently disclosed safety IV catheter assembly shown generally as 800. Catheter assembly 800 is similar to catheter assembly 700 in many respects and will be discussed in detail below.

Catheter assembly 800 comprises a needle assembly 810 including a needle hub 812 supporting a distally extending needle 818, a safety device 813 including a housing 814 and a biasing member 816, and a catheter assembly including a catheter hub 820 and a catheter tube 821 extending distally from the catheter hub 820. A proximal end of catheter hub 820 may include a luer connector 820a (FIG. 21) or the like for releasably securing the catheter hub 820 to a medical device such as a syringe. The needle hub 812 includes gripping surfaces 870 (FIG. 21) and the catheter hub 820 includes a finger engagement member 872 (FIG. 14). The finger engagement member 872 and the gripping surfaces 870 facilitate manipulation of the assembly 800 and assist in the separation of the catheter hub 820 from the safety device 813 and the needle assembly 810. The gripping surfaces 870 may be ribbed or include other known slip-resistant features. In a ready-to-use position or assembled state, the housing 814 of the safety device 813 is supported between the needle hub 812 and the catheter hub 820 and the needle 818 extends from the needle hub 812 through distal and proximal openings 824 and 826 of the safety device housing 814 and the catheter hub 820 such that a tip 818a of needle 818 projects from a distal end of the catheter tube 821.

Referring to FIGS. 14-17, the safety device 813 is similar to safety device 713 and includes housing 814 defining a cavity 831 supporting a biasing member 816. Housing 814 may be formed of molded half-sections which are joined together by snap-fitting, welding, or the like. The biasing member 816 includes a stationary portion 816a, a resilient arm or movable portion 816b, a blocking arm 816c and spring fingers 816d. The stationary portion 816a defines a series of openings 880 (FIG. 17) which receive posts 882 (FIG. 16) formed on an inner wall of housing 814 within cavity 831. The receipt of posts 882 within openings 880 properly positions and aligns the stationary portion 816a of the biasing member 816 within the housing 814. One or more of the posts 882 may be heat staked to secure the biasing member 816 to the posts 882. In addition, an elongated slot 866 (FIG. 17) is provided in stationary portion 816a of biasing member 816. Elongated slot 866 receives a rib 868 (FIG. 16) formed within housing 814 to also properly position and align biasing member 816 within cavity 831 of housing 814. Spring fingers 816d are received within a slot 860 (FIG. 15) defined within a C-channel 862 positioned in the cavity 831 of housing 814 to secure the biasing member 816 within the cavity 831 of housing 814. The inner wall of housing 814 also includes ribs 886 (FIG. 16) positioned on opposite sides of the needle 818 which restrict movement of the needle 818 during and after activation of the safety device 813.

As shown in FIG. 17, the blocking arm 816c is positioned to rest on one end of movable portion 816b when the movable portion 816b is in a deformed state engaged with needle 818. In one embodiment, the end of movable portion 816b includes one or more curved fingers 890 (FIG. 17) which engage the blocking arm 816c when the needle 818 is in an extended position and movable portion 816b is biased inwardly towards stationary portion 816a to the deformed state by the needle 818. When the needle tip 818a is withdrawn into housing 814 of the safety device 813 such that the needle tip 818a is pulled through the distal opening 824 (FIG. 20) of housing 814, the movable portion 816b of biasing member 816 springs outwardly from stationary portion 816a to a second position and tilts the housing 814 with respect to the needle tip 818a (FIG. 19) to misalign the distal opening 824 of housing 814 from the longitudinal axis of the needle 818. In the second position of movable portion 816b, the movable portion 816b contacts needle 818 and may still be in compression or may be unstressed. The proximal and or distal openings 826 and 824 of the safety device housing 814 may be oval shaped to facilitate tilting of the housing 814 in relation to the needle 818.

As shown in FIG. 20, when the movable portion 816b springs outwardly from stationary portion 816a, blocking arm 816c moves off of curved finger 890 downwardly to a position between stationary portion 816a and movable portion 816b (FIG. 20). In this position, the blocking arm 816c prevents the movable portion 816b from moving back to its deformed state (FIG. 16) to prevent the needle 818 from becoming realigned with the outlet opening 824.

In one embodiment, the portion of movable portion 816b of biasing member 816 which contacts the needle 818 is formed from or covered with a hard slick material 894 (FIG. 17A) to limit drag on the needle 818 as the needle 818 is withdrawn from the catheter hub 820 into the safety device 813. In one embodiment, the material covering the contacting portion of the biasing member is a UV cured adhesive. Alternately, other materials having a low coefficient of friction may be provided to cover or construct a portion of the movable portion 816b to allow needle 818 to move over movable portion 816b of biasing member with minimal friction or drag.

Figure 18:
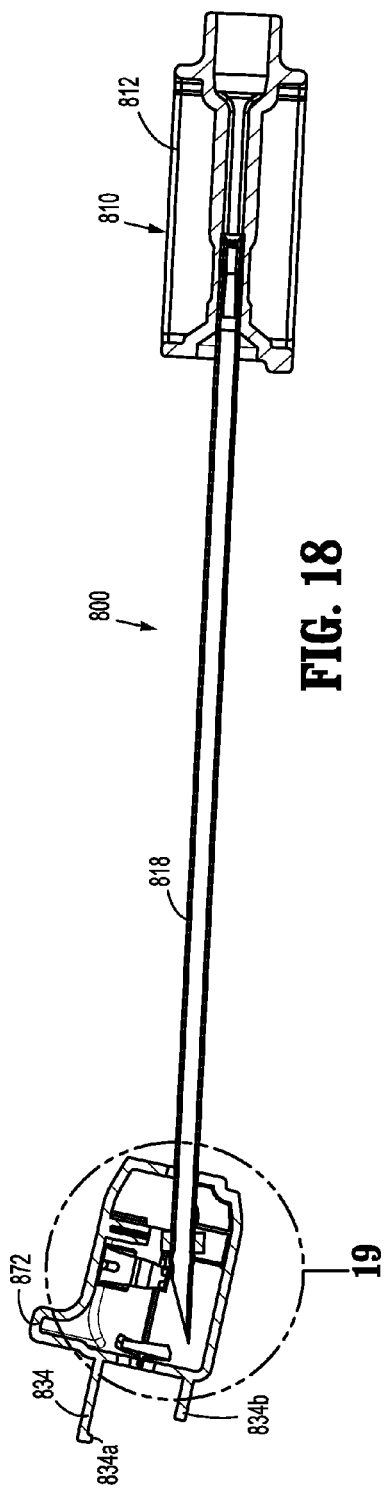
FIG. 18 is a side cross-sectional view of the safety IV catheter assembly in a disassembled state with the safety device supported on the distal end of the needle.
Figure 19:
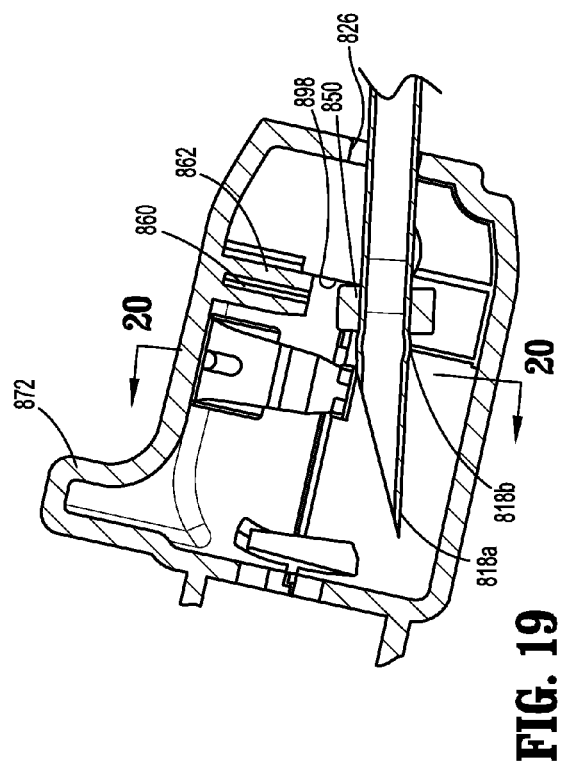
FIG. 19 is an enlarged view of the indicated area of detail shown in FIG. 18.
Figure 22:
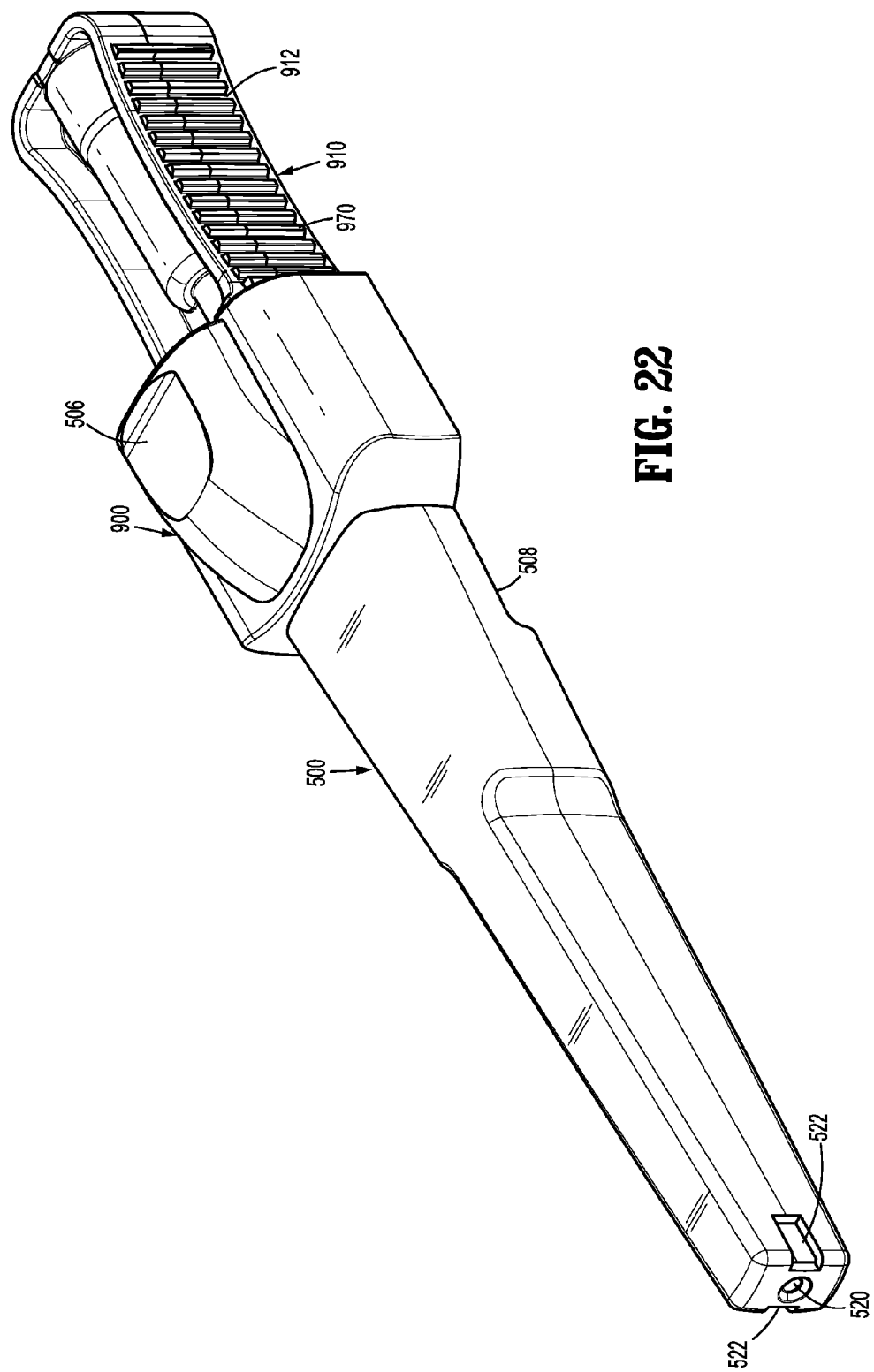
FIG. 22 is a side perspective view from the distal end of another alternate embodiment of the presently disclosed safety IV catheter assembly with a safety cover supported about the safety device and catheter assembly.
Figure 25:
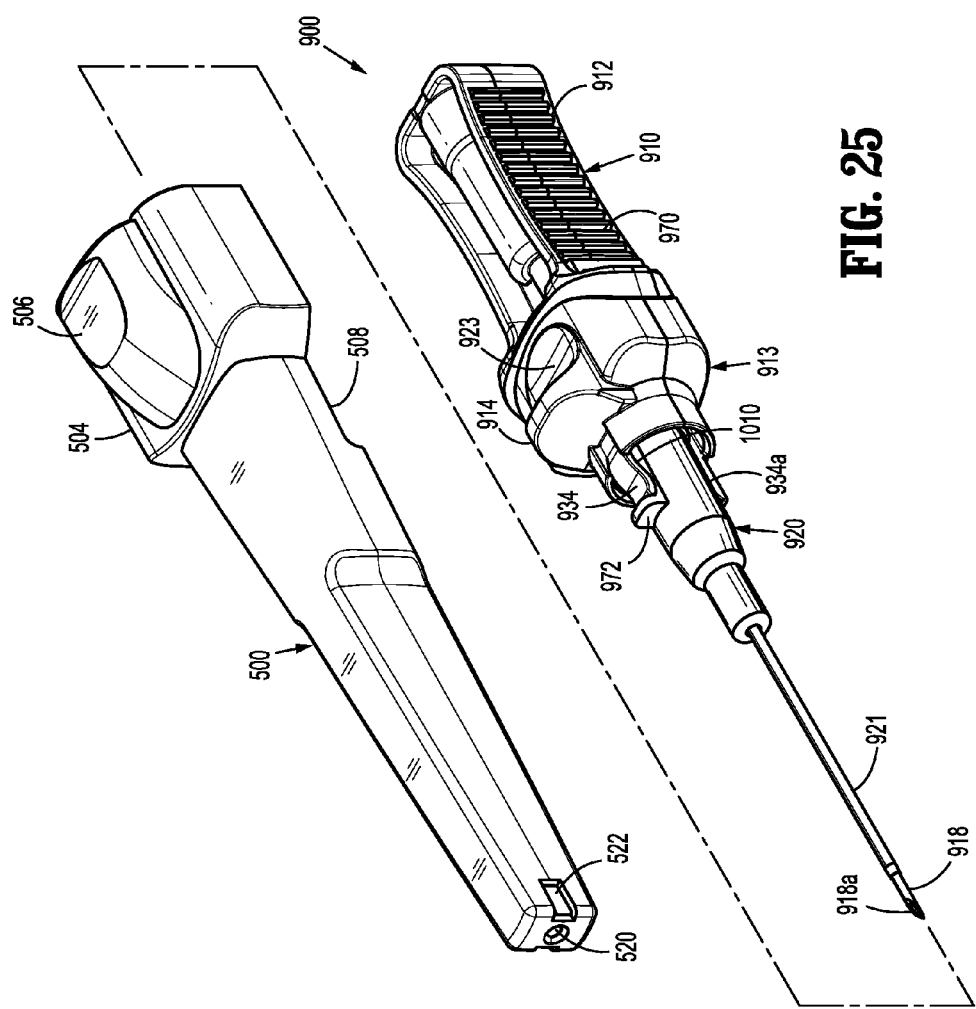
FIG. 25 is a top, perspective view from the distal end of the safety IV catheter shown in FIG. 22 with the safety cover separated from the IV catheter assembly.

As shown in FIGS. 18-19, needle 818 includes a crimp 818b and a bushing 850 positioned proximally of crimp 818b. The inside diameter of bushing 850 is larger than the outside diameter of needle 818 but smaller than the outside diameter of the crimp 818b such that bushing 850 is slidably disposed about needle 818 proximally of crimp 818b but cannot slide distally past the crimp 818b. At least one wall 898 (FIG. 19) is formed within cavity 831 of housing 814 which is positioned to allow withdrawal of needle 818 proximally from housing 814 of safety device but prevent passage of bushing 850. Thus, as needle 818 is being withdrawn through proximal opening 826 of housing 814, crimp 818b engages bushing 850 and retracts bushing 850 with needle 818 proximally until bushing 850 engages wall 898 of housing 814 of safety device 813. At this point, wall 898 prevents further proximal movement of bushing 850 and, thus, needle 818 to prevent further withdrawal of needle 818 through proximal opening 826 of housing 814 to safely retain needle tip 818a within housing 814 of safety device 813. In an alternative embodiment, the bushing 850 need not be provided and crimp 818 can be sized to prevent passage of needle 818 past wall 898 or through opening 826.

As shown in FIG. 18, housing 814 of safety device 813 also includes a finger 834 having a radial projection 834a which functions to releasably secure safety device 813 to catheter hub 820, and a tab 834b which properly orients the safety device 813 in relation to catheter hub 820 when the catheter assembly is in an assembled state. Finger 834 and tab 834b function in the same manner as finger 734 and tab 734b described above and will not be described in further detail herein.

FIGS. 22-40 illustrate an alternate embodiment of the presently disclosed safety IV catheter assembly shown generally as 900. Catheter assembly 900 is similar to catheter assemblies 700 and 800 in many respects and will be discussed in detail below.

Referring to FIGS. 22-28, catheter assembly 900 comprises a needle assembly 910 including a needle hub 912 supporting a distally extending needle 918, a safety device 913 including a housing 914 and a biasing member 916 (FIG. 28), and a catheter assembly including a catheter hub 920 and a catheter tube 921 extending distally from the catheter hub 920. A safety cover 500 is secured to the catheter hub 920 and encloses the catheter assembly 900 and needle tip 918a as will be discussed in further detail below.

Figure 28:
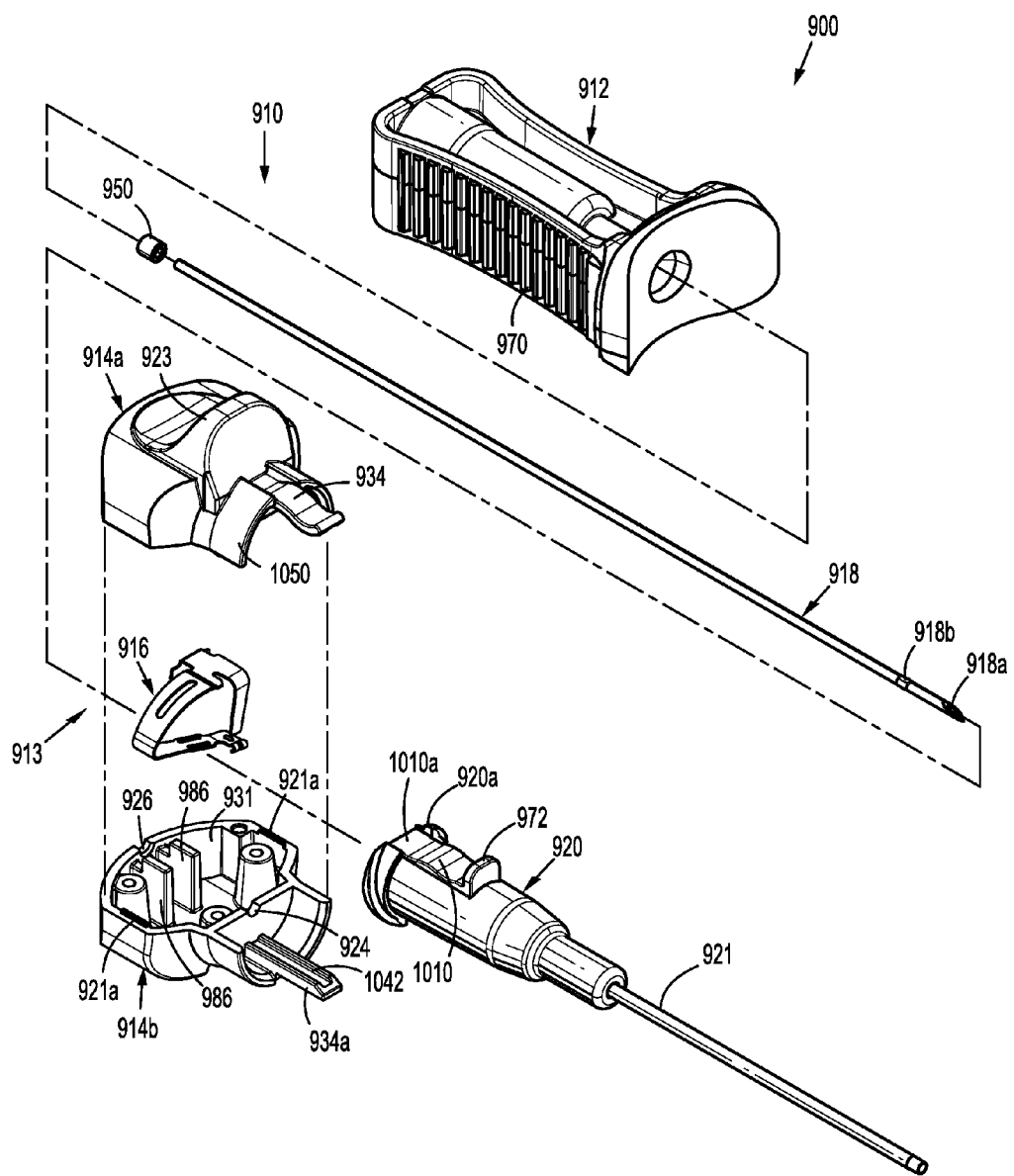
FIG. 28 is a side perspective view of the safety IV catheter assembly shown in FIG. 26 with parts separated.
Figure 29:
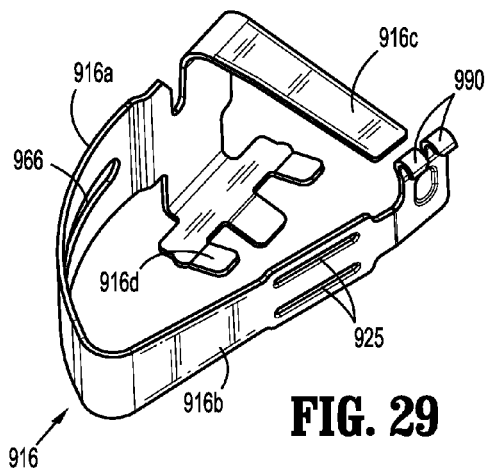
FIG. 29 is a top, perspective view of the biasing member of the safety device of the IV catheter assembly shown in FIG. 28.

Referring to FIGS. 25-28, a proximal end of catheter hub 920 may include a luer connector 920a (FIG. 28) or the like for releasably securing the catheter hub 920 to a medical device such as a syringe. The needle hub 912 includes gripping surfaces 970 (FIG. 22) and the catheter hub 920 includes a finger engagement member 972 (FIG. 27). The finger engagement member 972 and the gripping surfaces 970 facilitate manipulation of the safety IV catheter assembly 900 and assist in the manual separation of the catheter hub 920 from the safety device 913 and the needle assembly 910. The gripping surfaces 970 may be ribbed or include other known slip-resistant features. In addition, the needle hub 912 may be ergonomically configured to facilitate grasping by a clinician. For example, as shown in FIG. 28, the gripping surfaces 970 may have a non-linear, concave configuration.

In a ready-to-use position or assembled state (FIG. 25), the housing 914 of the safety device 913 is supported between the needle hub 912 and the catheter hub 920 and the needle 918 extends from the needle hub 912 through distal and proximal openings 924 and 926 (FIG. 30) of the safety device housing 914 and the catheter hub 920 such that a tip 918a of needle 918 projects from a distal end of the catheter tube 921.

Figure 35:
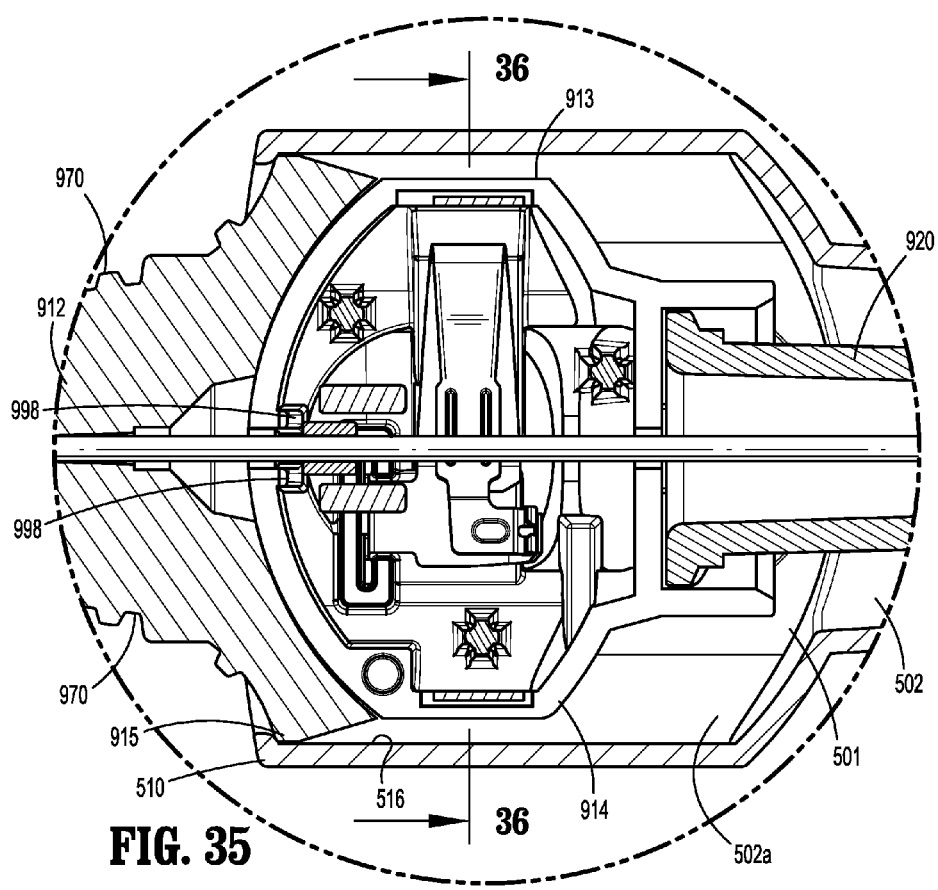
FIG. 35 is an enlarged view of the indicated area of detail shown in FIG. 34.

Referring to FIGS. 22-25 and 35, as discussed above, a safety cover 500 is releasably supported on the catheter hub 920 prior to use of the safety IV catheter assembly 900. The safety cover 500 defines an elongated receptacle 501 (FIG. 35) having a distal portion 502 dimensioned to receive the catheter assembly 900 and an enlarged proximal portion 502a dimensioned to receive a distal end of the needle hub 912 and the safety device 913. The proximal end 504 of the safety cover 500 which defines the proximal portion 502a of the receptacle 501 includes a raised hood 506 on one side and a cutout 508 on the other side. The raised hood 506 is dimensioned to receive a thumb engagement member 923 formed on the housing 914 of the safety device 913. A proximal edge 510 of the safety cover 500 is positioned to engage a distal ledge 915 (FIG. 35) formed on needle hub 912 to releasably secure safety cover 500 to needle hub 912. As shown in FIG. 35, the proximal portion of the receptacle 502a is dimensioned to receive the housing 914 of the safety device 913 in spaced relation such that the inner wall 516 of the safety cover 500 does not engage the housing 914. Such an arrangement minimizes the likelihood that removal of safety cover 500 from the safety IV catheter assembly will effect separation of the safety device 913 from the needle hub 912.

As shown in FIGS. 22-25, a distal end of the safety cover 500 defines a circular recess 520 and diametrically opposed notches 522. The circular opening 520 and notches 522 are provided to facilitate molding of the safety cover 500. More specifically, the circular opening 520 and notches 522 provide access for passage of a member (not shown) for stabilizing a core during a molding procedure.

Figure 40:
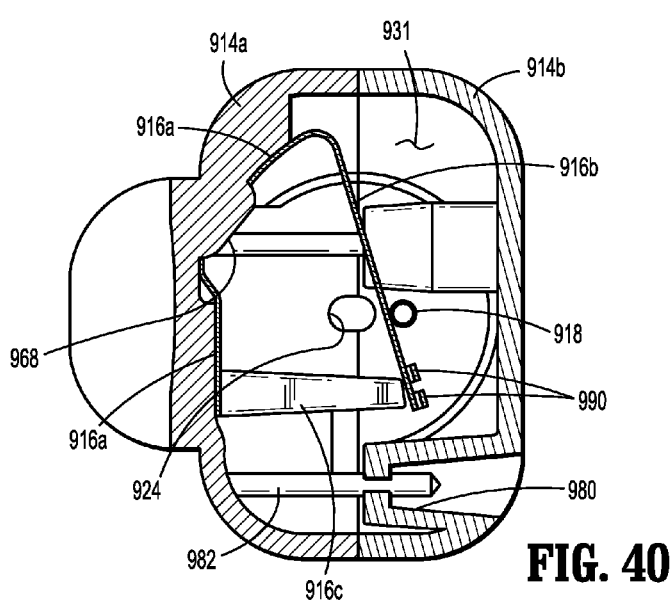
FIG. 40 is a cross-sectional view taken along section lines 40-40 of FIG. 39.

Referring to FIGS. 28-31, the safety device 913 is similar to safety device 813 and includes housing 914 defining a cavity 931 supporting a biasing member 916. Housing 914 may be formed of molded half-sections 914a and 914b (FIG. 28) which are joined together by snap-fitting, welding, or the like. In embodiments, one half-section 914a includes posts 982 which are heat staked within elongated openings 980 formed in the other half-section 914b to secure the housing half-sections together (FIG. 40). Alternately, the housing half-sections may be joined by ultrasonically welding the half-sections together. In one embodiment, half-section 914b includes recesses 921a (FIG. 28) which receive protrusions 921b (FIG. 30) on half-section 914a to properly align the half-sections prior to heat staking.

It is noted that the presently disclosed embodiments of the safety IV catheter are available in different sizes which include needle gauge sizes of 14, 16, 18, 20, 22 and 24. The size of the housing half-sections 914a and 914b are different in some respects for each size safety IV catheter. To ensure that a half-section 914a of one size is not inadvertently connected to a different size half-section 914b, the posts 982 and openings 980 or the protrusions 921b and recesses 921a may be selectively positioned to facilitate securement of only liked-sized half-sections and prevent securement of different sized half-sections.

The biasing member 916 may be formed from a single piece of resilient material such as spring steel or the like and includes a stationary portion 916a, a resilient arm or movable portion 916b, a blocking arm 916c and spring fingers 916d. Alternately, the biasing member may be formed from different components joined together using known fastening techniques. An elongated slot 966 (FIG. 29) is provided in stationary portion 916a of biasing member 916. Elongated slot 966 is dimensioned to receive a rib 968 (FIG. 30) formed within housing half-section 914a to properly position and align biasing member 916 within cavity 931 of housing 914. Spring fingers 916d are received within a slot 960 (FIG. 30) defined within a C-channel 962 positioned in the cavity 931 of housing 914 to secure the biasing member 916 within the cavity 931 of housing 914. The inner wall of housing 914b also includes ribs 986 (FIG. 28) positioned on opposite sides of the needle 918 which restrict movement of the needle 918 during and after activation of the safety device 913.

Figure 36:
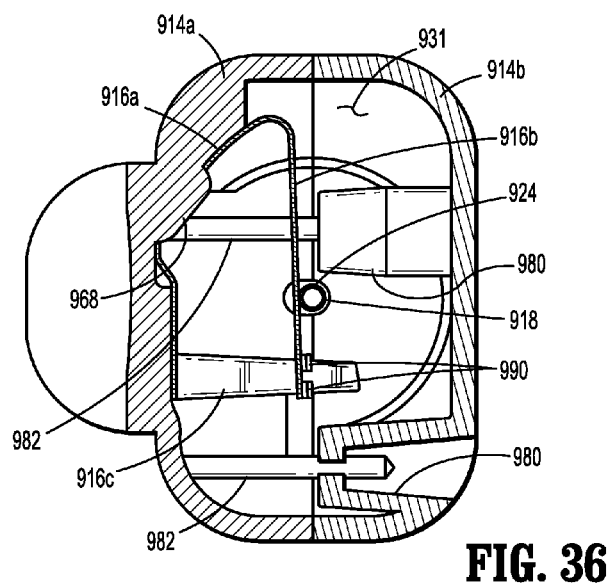
FIG. 36 is a cross-sectional view taken along section lines 36-36 of FIG. 35.
Figure 37:
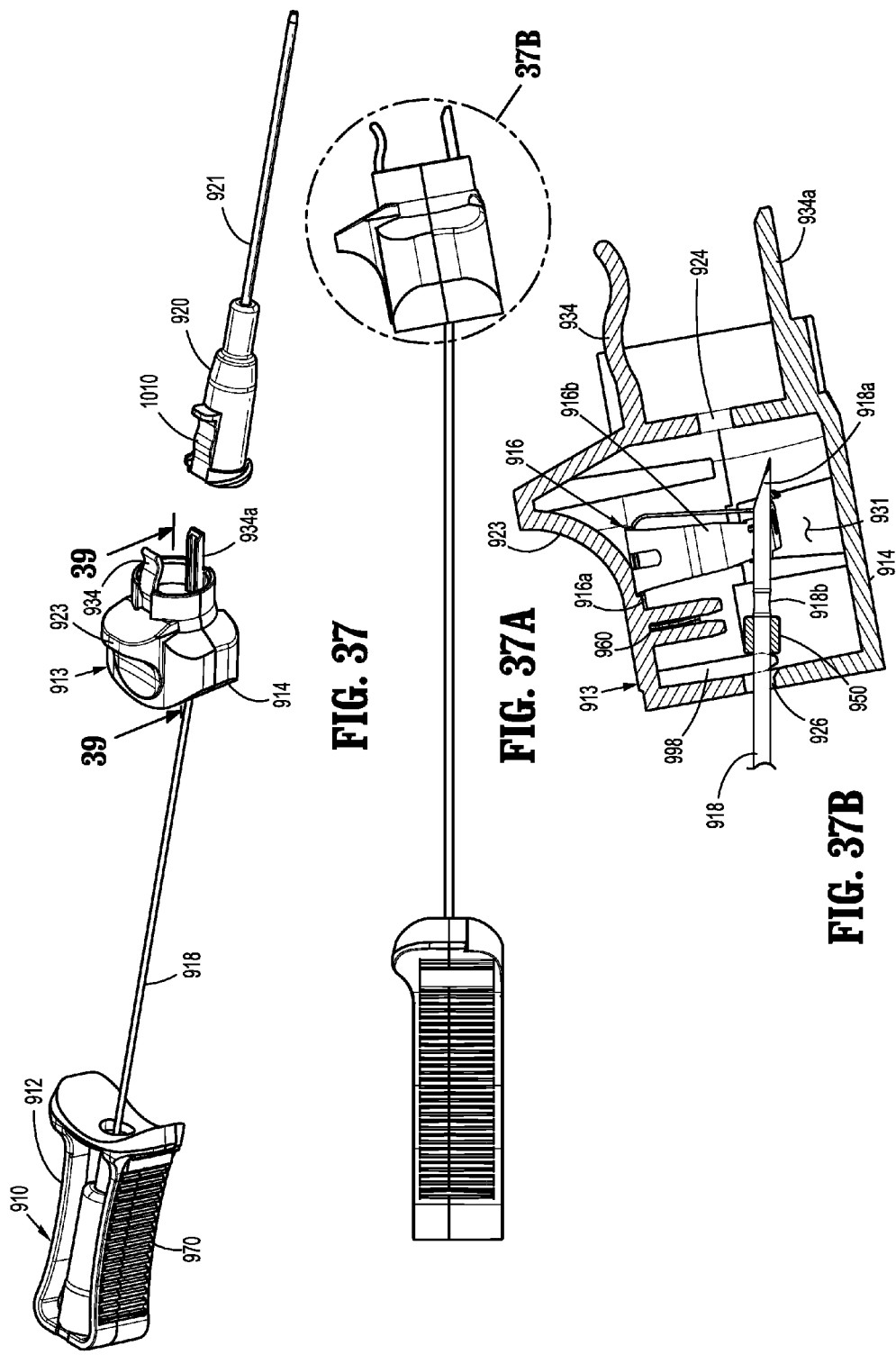
FIG. 37 is a side, perspective view of the IV catheter assembly with the needle assembly withdrawn from the catheter assembly and the safety device supported on the needle tip.

As shown in FIG. 36, the blocking arm 916c is positioned to rest on one end of movable portion 916b when the movable portion 916b is in a first position in a deformed state engaged with needle 918. In one embodiment, the end of movable portion 916b includes one or more curved fingers 990 (FIG. 29) which engage the blocking arm 916c when the needle 918 is in an extended position and movable portion 916b is biased inwardly towards stationary portion 916a to the deformed state by the needle 918. As shown in FIG. 37-37B, when the needle tip 918a is withdrawn into cavity 931 of housing 914 of the safety device 913 such that the needle tip 918a is pulled through the distal opening 924 (FIG. 39) of housing 914, the movable portion 916b of biasing member 916 springs outwardly from stationary portion 916a from the first position along a path of movement to a second position and tilts the housing 914 with respect to the needle tip 918a (FIG. 37b) to misalign the distal opening 924 of housing 914 from the longitudinal axis of the needle 918. In the second position of movable portion 916b, the movable portion 916b contacts needle 918 and may still be in compression or may be unstressed. The proximal and/or distal openings 926 and 924 of the safety device housing 914 may be oval shaped to facilitate tilting of the housing 914 in relation to the needle 918.

As shown in FIG. 40, when the movable portion 916b springs outwardly from stationary portion 916a, blocking arm 916c moves off of curved fingers 990 downwardly to a position between stationary portion 916a and movable portion 916b (see also FIG. 28). In this position, the blocking arm 916c prevents the movable portion 916b from moving back to its deformed state to prevent the needle 918 from becoming realigned with the outlet opening 924.

As discussed above with regard to biasing member 816, a portion of movable portion 916b of biasing member 916 which contacts the needle 918 may be formed from or covered with a hard slick material, such as a UV cured adhesive, (FIG.) to limit drag on the needle 918 as the needle 918 is withdrawn from the catheter hub 920 into the safety device 913. Alternately, other materials having a low coefficient of friction may be provided to cover or construct a portion of the movable portion 916b of biasing member 916 to allow needle 918 to move over movable portion 916b of biasing member with minimal friction or drag. In addition, the movable portion 916b may include one or more ribs 925 (FIG. 29) positioned to engage the needle 918 to minimize drag on the needle 918.

Figure 38:
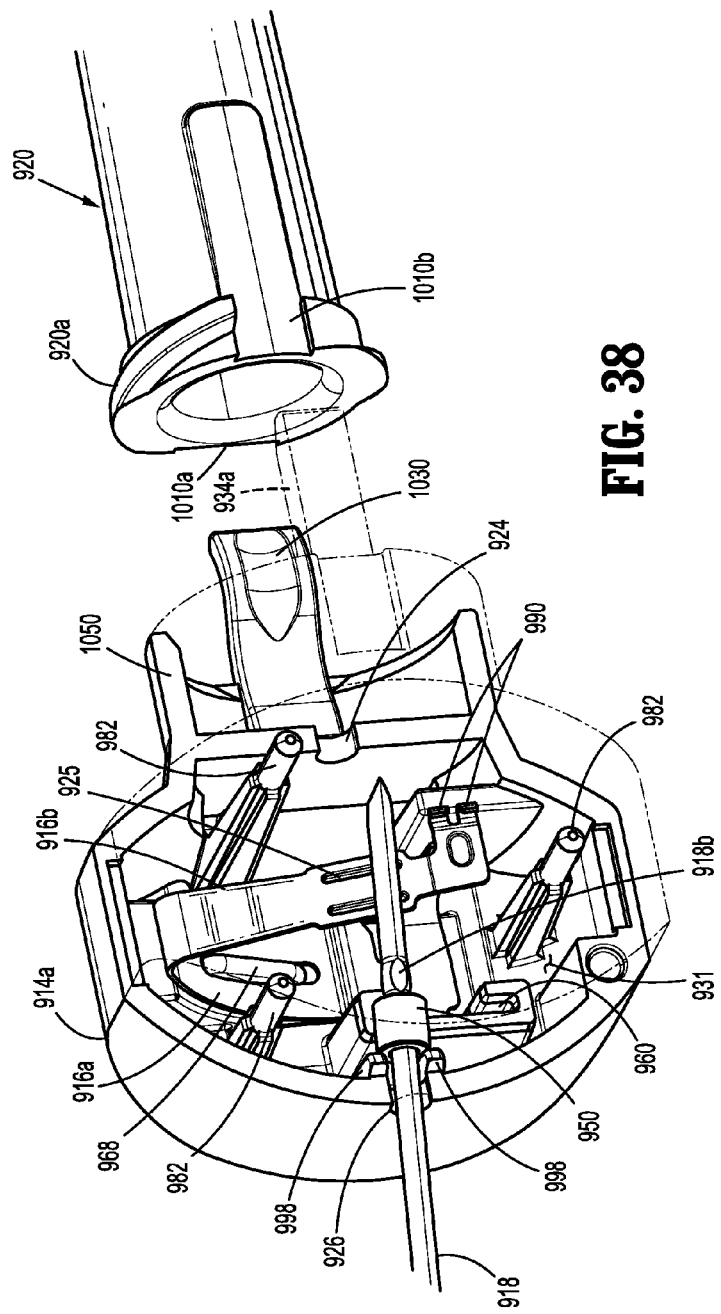
FIG. 38 is a side perspective view of the distal end of the needle with the needle tip positioned within the safety device housing with a housing half-section of the safety device removed.
Figure 39:
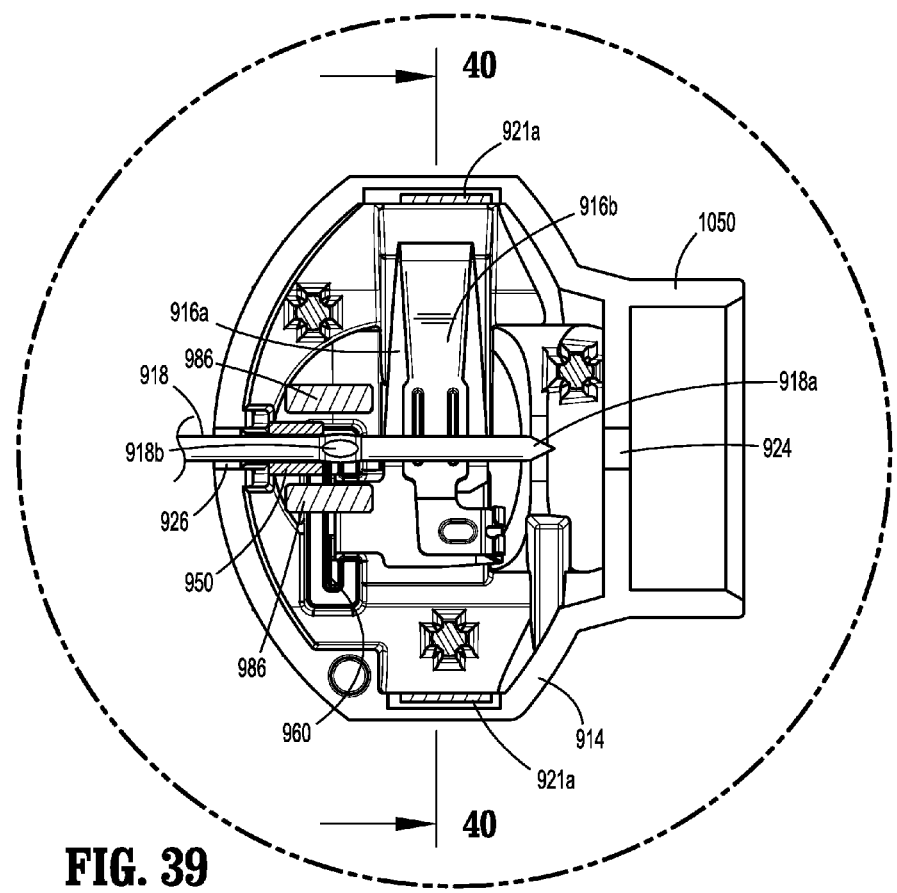
FIG. 39 is a side-partial cross-sectional view of the safety device and distal end of the needle of the safety IV catheter assembly shown in FIG. 38.

As shown in FIGS. 28, 38 and 39, needle 918 includes a crimp 918b and a bushing 950 positioned proximally of crimp 918b. The inside diameter of bushing 950 is larger than the outside diameter of needle 918 but smaller than the outside diameter of the crimp 918b such that bushing 950 is slidably disposed about needle 918 proximally of crimp 918b but cannot slide distally past the crimp 918b. At least one wall 998 (FIG. 38) is formed within cavity 931 of housing 914 which is positioned to allow withdrawal of needle 918 proximally from housing 914 of safety device but prevent passage of bushing 950. Thus, as needle 918 is being withdrawn through proximal opening 926 of housing 914, crimp 918b engages bushing 950 and retracts bushing 950 with needle 918 proximally until bushing 950 engages wall 998 of housing 914 of safety device 913. At this point, wall 998 prevents further proximal movement of bushing 950 and, thus, needle 918 to prevent further withdrawal of needle 918 through proximal opening 926 of housing 914 to safely retain needle tip 918a within housing 914 of safety device 913. In an alternative embodiment, the bushing 950 need not be provided and crimp 918 can be sized to prevent passage of needle 918 past wall 998 or through opening 926.

Figure 33:
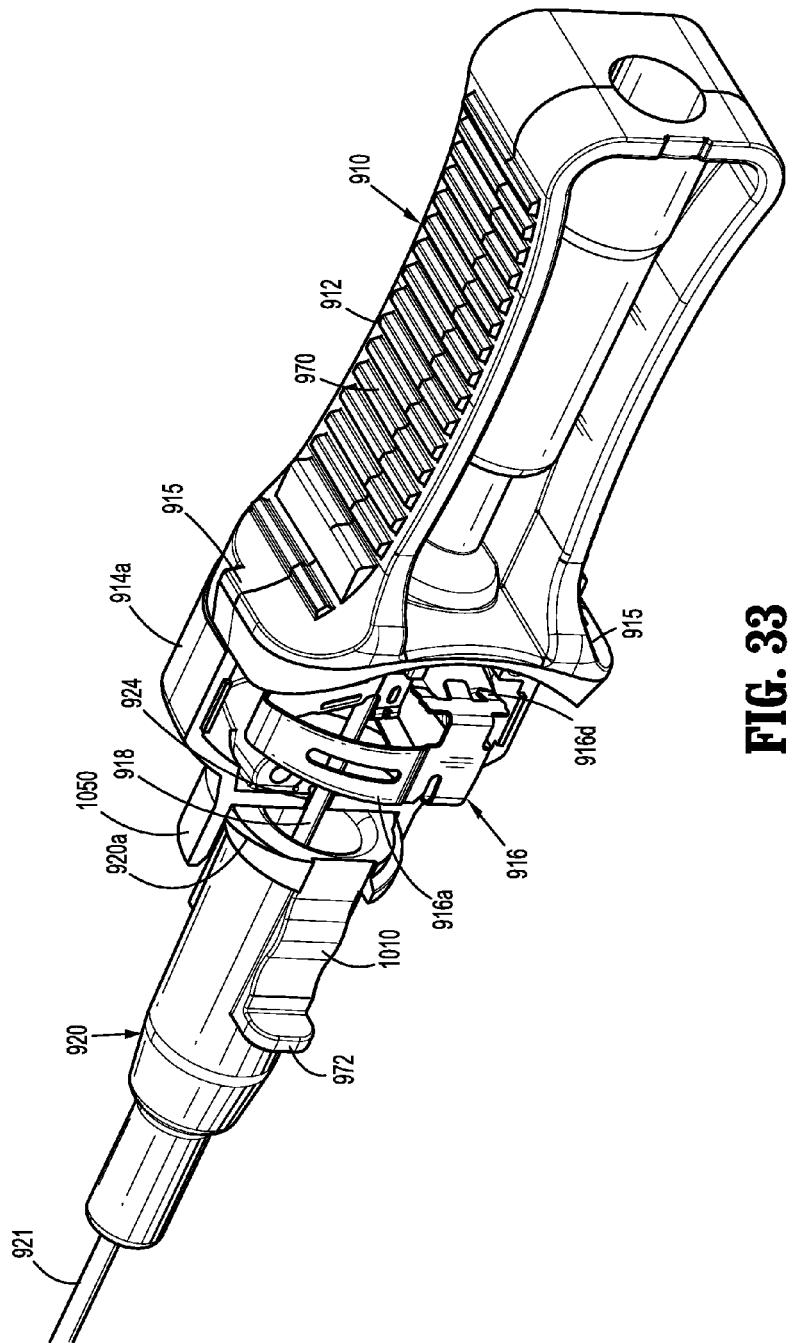
FIG. 33 is a side perspective view of the IV catheter assembly shown in FIG. 32 with the other housing half-section removed from the safety device.
Figure 34:
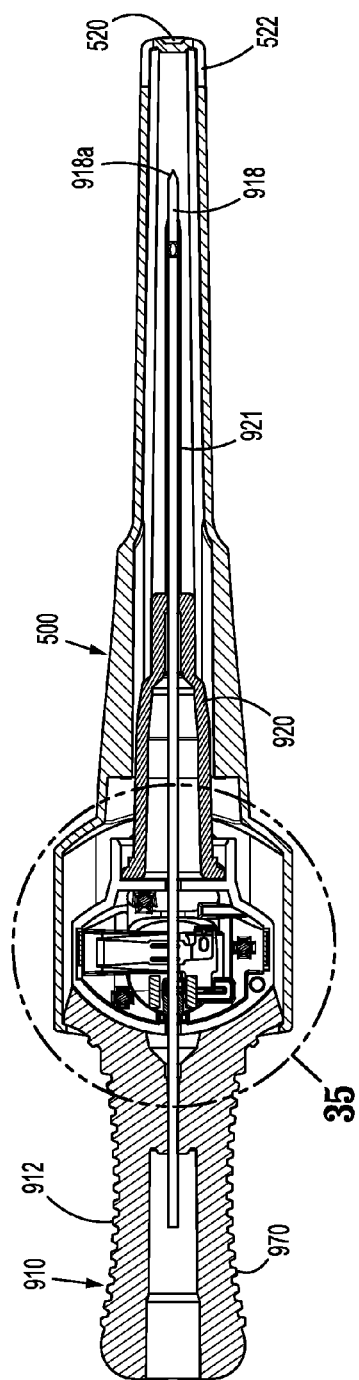
FIG. 34 is a side cross-sectional view of the IV catheter assembly and safety cover taken along section lines 34-34 of FIG. 23.

As best shown in FIGS. 27, 28 and 33, the housing half-section 914a of the safety device 913 includes a curvilinear or radiused finger 934 which is positioned to engage a curvilinear or radiused surface 1010 formed on the catheter hub 920 to releasably secure the catheter hub 920 to the safety device 913. Curvilinear surface 1010 extends through a cutout 1010a formed through the luer connector 920a. In one embodiment, each of the radiused finger 934 and the radiused surface 1010 includes two or more curvilinear sections which have different radiuses of curvature. By providing different radiuses of curvature on the radiused finger 934 and the radiused surface 1010, finger 934 is able to engage the surface 1010 at four points of contact to secure the catheter hub 920 to the safety device housing 914.

Figure 30:
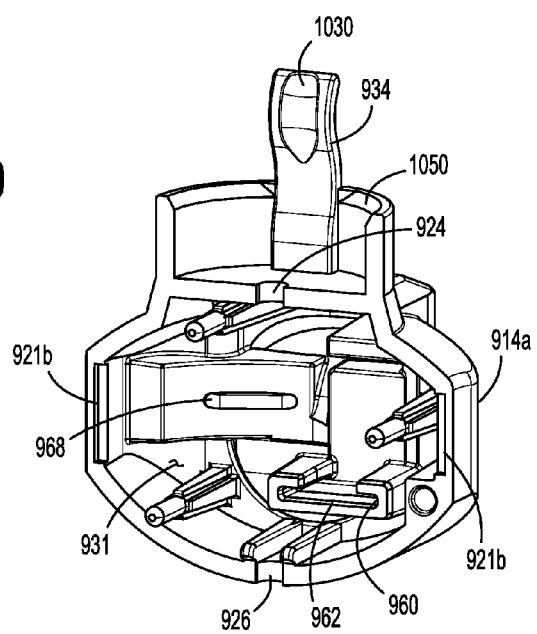
FIG. 30 is a side perspective view of a housing half-section of the safety device shown in FIG. 28 with the biasing member removed.
Figure 31:
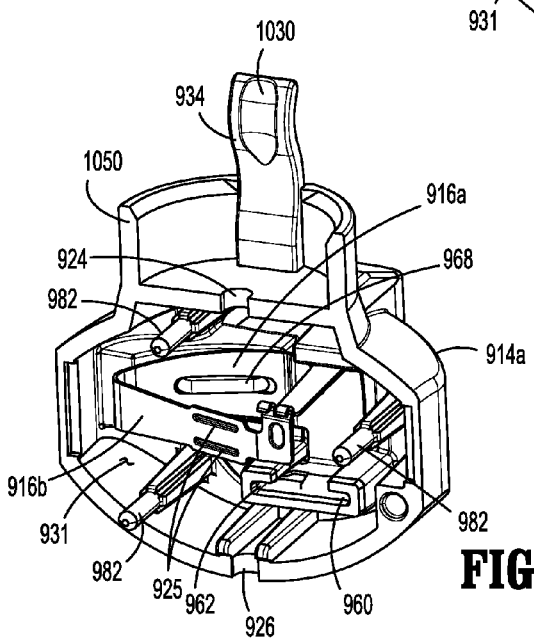
FIG. 31 is a side perspective view of the housing half-section shown in FIG. 30 with the biasing member positioned in the housing half-section.
Figure 32:
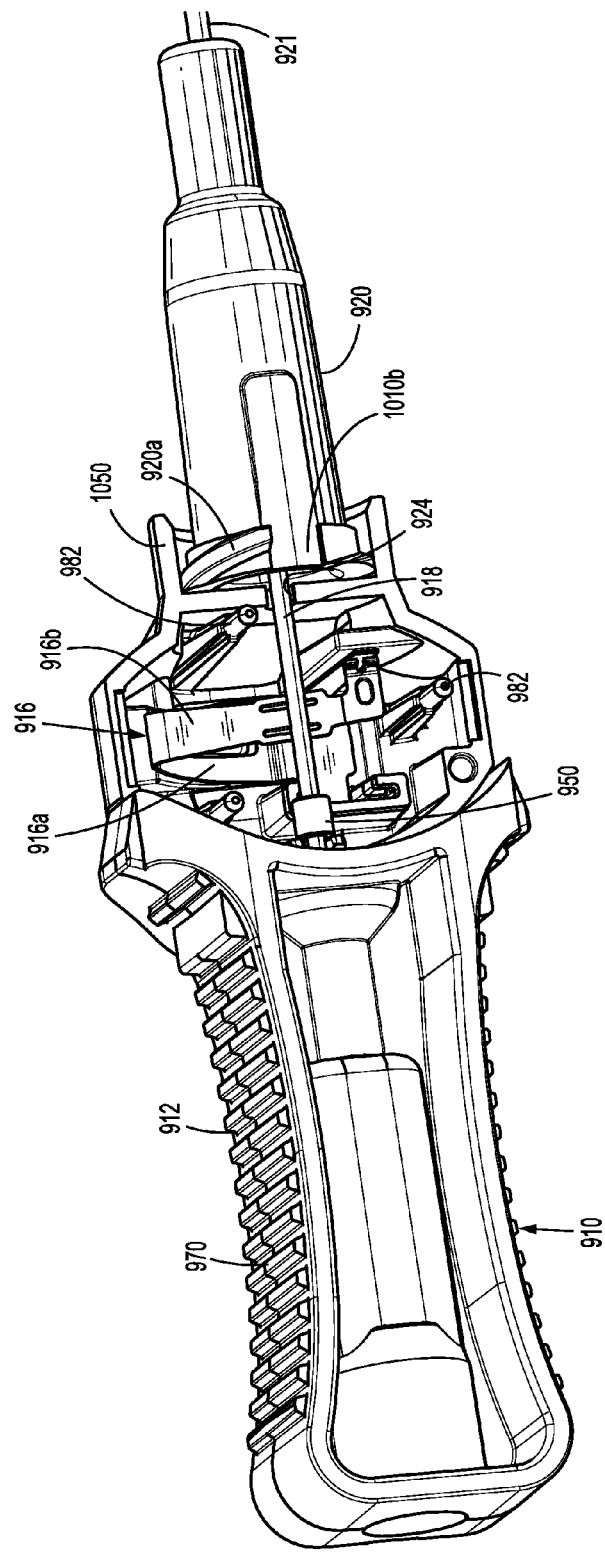
FIG. 32 is a side perspective view of the IV catheter assembly shown in FIG. 26 in an assembled state with one housing half-section removed from the safety device.

As illustrated in FIG. 38, a bottom surface of radiused finger 934 includes a centrally located recess 1030 (FIG. 30). Recess 1030 minimizes the contact surface area between finger 934 and surface 1010 of catheter hub 920 to reduce friction during separation of the catheter hub 920 from the housing 914 of the safety device 913.

Referring to FIGS. 27 and 28, the housing 914 of the safety device 913 also includes a linear finger or tab 934a. Tab 934a extends through a second cutout 1010b formed through the luer connector 920a and is positioned to engage a side of the catheter hub 920 opposite to the radiused surface 1010. Tab 934a functions to press the catheter hub 920 against the radiused finger 934 to provide support to the catheter hub 920. The inner surface of tab 934a includes a central channel 1042 (FIG. 28). As such, only the outer edges of tab 934a engage the catheter hub 920 at locations outwardly of the centerline of the catheter hub 920. The housing 914 of the safety device 913 also includes an annular body portion 1050 which surrounds the proximal end of the catheter hub 920 including the luer connector 920a to further stabilize the catheter hub 920 in relation to the safety device 913.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A safety intravenous catheter assembly comprising:
   a needle assembly including a needle hub and a needle having a proximal end secured to the needle hub and a distal end defining a tip;
   a catheter assembly including a catheter hub and a catheter tube extending distally from the catheter hub; and
   a safety device including a housing defining a cavity, a distal opening and a proximal opening and a biasing member supported within the cavity, the distal and proximal openings being dimensioned to receive the needle, the biasing member including a stationary portion, a movable portion and a blocking arm, the movable portion being movable in relation to the stationary portion along a path of movement from a first position to a second position;
   wherein in an assembled state, the safety device is positioned between the needle hub and the catheter hub, the needle extends through the proximal and distal openings of the housing of the safety device and the catheter assembly, the biasing member is compressed between the needle and the housing such that the movable portion is in the first position in engagement with the needle and the blocking arm is spaced outwardly of the path of movement of the movable portion, and in a disassembled state, the tip of the needle is withdrawn through the distal opening into the cavity of the housing of the safety device and the movable portion of the biasing member is in the second position spaced further outwardly of the stationary portion such that the housing is tilted in relation to the needle to move the needle out of alignment with the distal opening of the housing, wherein in the disassembled state, the blocking arm is positioned between the movable portion and the stationary portion to prevent movement of the movable portion from the second position back to the first position.

2. The catheter assembly of claim 1, wherein the housing includes at least one post extending from one side of the housing across the cavity, the post being positioned to engage the stationary portion of the biasing member to secure the position of the biasing member within the housing.

3. The catheter assembly of claim 2, wherein the housing is formed from molded half-sections, the at least one post being formed on one of the half-sections and extending across the cavity towards a sidewall of the other of the half-sections.

4. The catheter assembly of claim 1, wherein the housing of the safety device includes a finger configured to releasably engage the catheter hub.

5. The catheter assembly of claim 4, wherein the finger includes radial projection which is configured to be received in a recess formed in the catheter hub to releasably secure the safety device to the catheter hub.

6. The safety device of claim 4, wherein the finger is radiused and is positioned to releasably engage a radiused surface on the catheter hub.

7. The safety device of claim 6, wherein the radiused finger has a different radius of curvature than the radius of curvature of the radiused surface on the catheter hub.

8. The safety device of claim 6, further including a second finger on the housing of the safety device positioned to engage a side of the catheter hub opposite to the radiused surface.

9. The catheter assembly of claim 1, wherein the biasing member is unitarily formed from a resilient material.

10. The catheter assembly of claim 9, wherein the resilient material is spring steel.

11. The catheter assembly of claim 1, wherein the needle hub includes a tab and the housing of the safety device defines a cutout positioned to receive the tab to properly orient the safety device in relation to the needle hub when the catheter assembly is in the assembled state.

12. The catheter assembly of claim 1, wherein the proximal end of the catheter hub defines a luer connector.

13. The catheter assembly of claim 1, wherein the portion of the movable portion of the biasing member in engagement with the needle includes a material having a low coefficient of friction.

14. A safety intravenous catheter assembly comprising:
    a needle assembly including a needle hub and a needle having a proximal end secured to the needle hub and a distal end defining a tip;
    a catheter assembly including a catheter hub and a catheter tube extending distally from the catheter hub; and
    a safety device including a housing defining a cavity, a distal opening and a proximal opening and a biasing member supported within the cavity, the distal and proximal openings being dimensioned to receive the needle, the biasing member including a stationary portion, a movable portion and a blocking arm, the movable portion being movable in relation to the stationary portion from a first position to a second position;
    wherein in an assembled state, the safety device is positioned between the needle hub and the catheter hub, the needle extends through the proximal and distal openings of the housing of the safety device and the catheter assembly, and the biasing member is compressed between the needle and the housing such that the movable portion is in the first position in engagement with the needle, and in a disassembled state, the tip of the needle is withdrawn through the distal opening into the cavity of the housing of the safety device and the movable portion of the biasing member is in the second position spaced further outwardly of the stationary portion such that the housing is tilted in relation to the needle to move the needle out of alignment with the distal opening of the housing, wherein in the disassembled state, the blocking arm is positioned between the movable portion and the stationary portion to prevent movement of the movable portion from the second position back to the first position, wherein the portion of the movable portion of the biasing member in engagement with the needle is at least partially covered by a UV cured adhesive.

15. A safety device comprising:
    a housing defining a cavity having a distal opening and a proximal opening, the distal and proximal openings being dimensioned to receive a needle of an intravenous catheter assembly; and
    a biasing member supported within the cavity, the biasing member having a stationary portion, a movable portion, and a blocking arm, the movable portion being movable in relation to the stationary portion along a path of movement from a first position in which the biasing member is compressed between the needle and the housing to a second position in which the movable portion is spaced further outwardly of the stationary portion to tilt the housing in relation to the needle and move the needle out of alignment with the distal opening of the housing;
    wherein as the movable portion moves from the first position to the second position, the blocking arm moves from a position spaced outwardly of the path of movement of the movable portion to a position in the path of movement of the movable portion to prevent movement of the movable portion from the second position back to the first position.

16. The safety device of claim 15, wherein the housing includes at least one post extending from one side of the housing across the cavity, the at least one post being positioned to engage the stationary portion of the biasing member.

17. The safety device of claim 15, wherein the housing of the safety device includes a finger configured to releasably engage a catheter hub.

18. The safety device of claim 17, wherein the finger is radiused.

19. The safety device of claim 15, wherein the biasing member is unitarily formed from a resilient material.

20. The safety device of claim 15, wherein the housing is formed from molded half-sections.

21. The safety device of claim 15, wherein the portion of the movable portion of the biasing member in engagement with the needle includes a material having a low coefficient of friction.

* * * * *